United States Patent
Thalhamer et al.

(10) Patent No.: US 11,020,477 B2
(45) Date of Patent: Jun. 1, 2021

(54) RNA VACCINES

(71) Applicant: BIONTECH RNA PHARMACEUTICALS GMBH, Mainz (DE)

(72) Inventors: Josef Thalhamer, Lamprechtshausen (AT); Richard Weiss, Salzburg (AT); Elisabeth Rosler, Salzburg (AT); Sandra Scheiblhofer, Salzburg (AT); Angelika Fruhwirth, Innsbruck (AT)

(73) Assignee: BIONTECH RNA PHARMACEUTICALS GMBH, Mainz (DE)

( * ) Notice: Subject to any disclaimer, the term of this patent is extended or adjusted under 35 U.S.C. 154(b) by 0 days.

(21) Appl. No.: 15/410,807

(22) Filed: Jan. 20, 2017

(65) Prior Publication Data
US 2017/0136121 A1    May 18, 2017

Related U.S. Application Data

(60) Division of application No. 14/026,436, filed on Sep. 13, 2013, now abandoned, which is a continuation of application No. 12/680,354, filed as application No. PCT/EP2008/063035 on Sep. 29, 2008, now abandoned.

(30) Foreign Application Priority Data

Sep. 28, 2007 (EP) ..................... 07450169

(51) Int. Cl.
| | |
|---|---|
| *A61K 39/36* | (2006.01) |
| *A61K 38/20* | (2006.01) |
| *A61K 39/35* | (2006.01) |
| *C12N 7/00* | (2006.01) |
| *A61K 39/00* | (2006.01) |

(52) U.S. Cl.
CPC ............ *A61K 39/36* (2013.01); *A61K 38/208* (2013.01); *A61K 38/2086* (2013.01); *A61K 39/35* (2013.01); *C12N 7/00* (2013.01); *A61K 2039/53* (2013.01); *A61K 2039/55522* (2013.01); *A61K 2039/55561* (2013.01); *A61K 2039/57* (2013.01); *A61K 2039/575* (2013.01); *C12N 2770/36143* (2013.01)

(58) Field of Classification Search
None
See application file for complete search history.

(56) References Cited

U.S. PATENT DOCUMENTS

| | | | | |
|---|---|---|---|---|
| 5,580,859 A | * | 12/1996 | Felgner ................ | A61K 9/1272 435/69.1 |
| 2003/0202980 A1 | | 10/2003 | Caplan et al. | |
| 2004/0033585 A1 | * | 2/2004 | McCormick ........... | A61K 39/12 435/235.1 |
| 2005/0154189 A1 | * | 7/2005 | Punnonen ........ | C07K 14/70503 530/350 |
| 2008/0025944 A1 | * | 1/2008 | Hoerr ...................... | A61P 37/06 424/85.2 |
| 2011/0033416 A1 | | 2/2011 | Thalhamer et al. | |

FOREIGN PATENT DOCUMENTS

| | | |
|---|---|---|
| EP | 1224215 | 10/2000 |
| EP | 1440979 | 1/2003 |
| JP | 10-510246 | 10/1998 |
| WO | WO 95/21931 | 1/1995 |
| WO | WO96/25508 | 2/1996 |
| WO | WO 09/040443 | 4/2009 |

OTHER PUBLICATIONS

Niederberger et al., Vaccination with genetically engineered allergens prevents progression of allergic disease; PNAS, vol. 101, No. 2, pp. 14677-14682, 2004.*
Printout of the Webster's definition of 'Excipient'; https://www.dictionary.com/browse/excipient?s=t; Accessed Sep. 9, 2019. (Year: 2019).*
Printout of the Wikipedia article on pharmaceutical excipients; (http://en.wikipedia.org/wiki/Excipient: accessed Sep. 9, 2019. (Year: 2019).*
Vollmer et al., Characterization of three oligodeoxynucleotide classes with distinct immunostimulatory activities; Eur. J. Immunol. vol. 34, pp. 251-262, 2004 (Year: 2004).*
Valenta et al., "Recombinant allergens" 53 Allergy 552-561 (1998).*
Rupa et al., "Immunological comparison of native and recombinant egg allergen, ovalbumin, expressed in *Escherichia coli*" 25 Biotechnology Letters 1917-1924 (2003).*
Bauer, et al., "Generation of hypoallergenic DNA vaccines by forced ubiquitination: Preventive and therapeutic effects in a mouse model of allergy," *Journal of Allergy and Clinical Immunology* (2006) 118/1 :269-276.
Ford, et al., "IL-13 and IFN-{gamma}: Interactions in Lung Inflammation," *J Immunol.* (2001) 167:1769-1777.
Gabler, et al., "Immunization with a low-dose replicon DNA vaccine encoding Phl p 5 effectively prevents allergic sensitization," *J Allergy Clin Immunol.* (2006) 118:734-41.
Hartl, A., et al., "DNA vaccines for allergy treatment," *Methods: A companion to Methods in Enztmology* (2004) 32/3:328-339.
Linhart, et al., "Vaccine Engineering Improved by Hybrid Technology," *International Archives of Allergy and Immunology* (2004) 134(4):324-331.

(Continued)

*Primary Examiner* — Nancy J Leith
(74) *Attorney, Agent, or Firm* — Saliwanchik, Lloyd & Eisenschenk

(57) ABSTRACT

A RNA vaccine containing a RNA molecule encoding an allergen or derivative thereof, in which the allergen is an allergen of *Alnus glutinosa, Alternaria alternata, Ambrosia artemisiifolia, Apium graveolens, Arachis hypogaea, Betula verrucosa, Carpinus betulus, Castanea sativa, Cladosporium herbarum, Corylus avellana, Cryptomeria japonica, Cyprinus carpio, Daucus carota, Dermatophagoides pteronyssinus, Fagus sylvatica, Felis domesticus, Hevea brasiliensis, Juniperus ashei, Malus domestica, Quercus alba* or *Phleum pratense*.

14 Claims, 17 Drawing Sheets
Specification includes a Sequence Listing.

(56) References Cited

OTHER PUBLICATIONS

Nair, S.K., et al., "Induction of Primary Carcinoembryonic Antigen (CEA)-Specific Cytotoxic T Lymphocytes in Vitro Using Human Dendritic Cells Transfected with RNA," *Nature Biotechnology* (1998) 16/4:364-369.

Tang, et al., "Genetic immunization is a simple method for eliciting an immune response," *Nature* (1992) 356:152-154.

Weiss, et al., "Is Genetic Vaccination against Allergy Possible?" *Int Arch Allergy Immunol.* (2006) 139:332-345.

Ying, et al., "Cancer Therapy Using a Self-Replicating RNA Vaccine," *Nature Medicine* (1999) 5:823-827.

Zhou, et al., "Self-Replicating Semliki Forest Virus RNA as Recombinant Vaccine," *Vaccine* (1994) pp. 1510-1514.

JP2010-526322: Office Action dated May 14, 2013 and English translation.

Carralot, J.P., et al., "Polarization of immunity induced by direct injection of naked sequence-stabilized mRNA vaccines," CMLS, *Cell. Mol. Life Sci.* 61(2004) pp. 2418-2424.

Gabler, M., et al., "Immunization with a low-dose replicon DNA vaccine encoding Phl p 5 effectively prevents allergic sensitization," *J Allergy Clin Immunol* (Sep. 2006) vol. 118, No. 3, pp. 734-741.

Japanese Journal of Pediatrics (2000), vol. 53, pp. 617-621.

Modern Physician, (2002), vol. 22, No. 2, pp. 213-217.

Pascolo, S. "Messenger RNA-based vaccines," *Expert Opin Bio Ther* (2004) vol. 4, No. 8, pp. 1285-1294.

Santilez et al., "Amb a 1-linked CpG oligodeoxynucleotides reverse established airway hyperresponsiveness in a murine model of asthma," *J Allergy Clin Immunol*, vol. 108, No. 8, pp. 455-462, 2002.

Holtkamp et al., "Modification of antigen-encoding RNA increases stability, translational efficacy and T-cell stimulatory capacity of dendritic cells," *Blood*, vol. 108, No. 13, pp. 4009-4017, 2006.

Pardi, N. et al. "mRNA vaccines—a new era in vaccinology" *Nature Reviews Drug Discovery*, Apr. 2018, pp. 261-278, vol. 17.

Hoerr, I. et al. "In vivo application of RNA leads to induction of specific cytotoxic T lymphocytes and antibodies" *Eur. J. Immunol.*, 2000, pp. 1-7, vol. 30.

\* cited by examiner

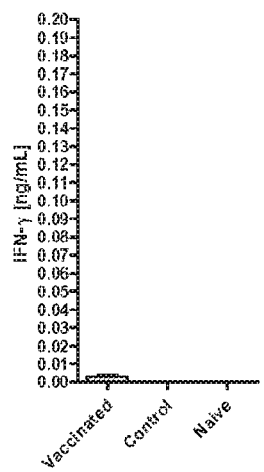 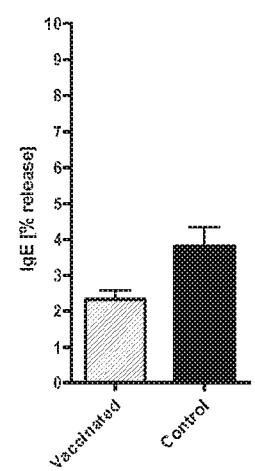
Fig. 16A        Fig. 16B
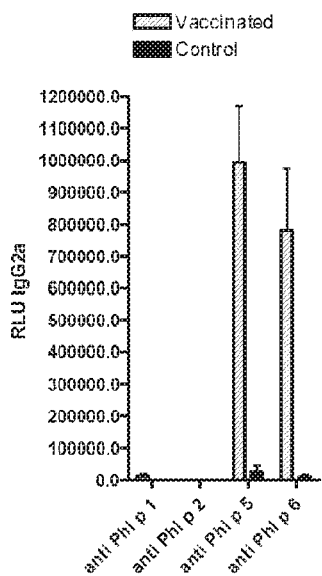 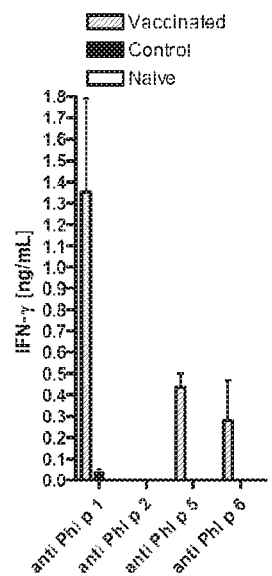 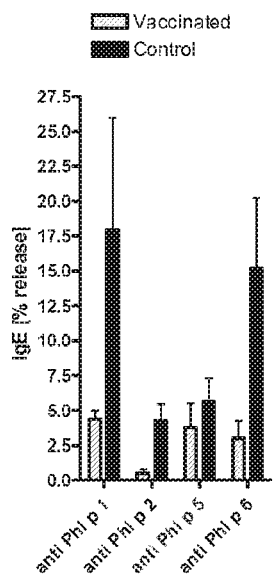
Fig. 17A        Fig. 17B        Fig. 17C

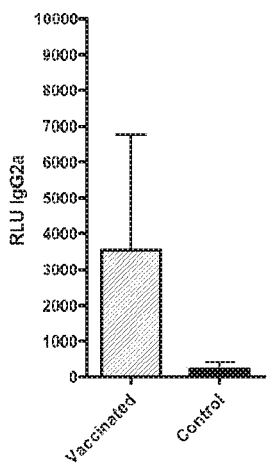
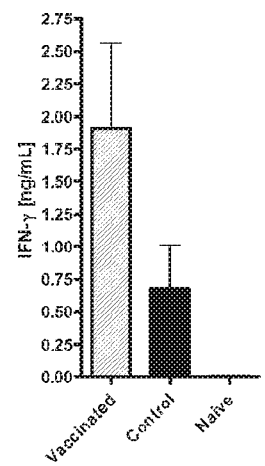
Fig. 18A        Fig. 18B
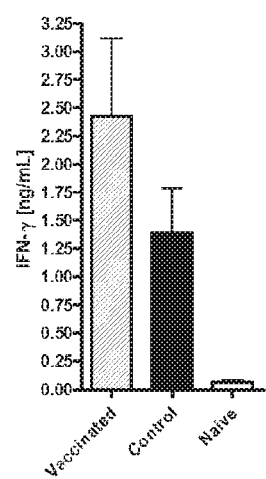
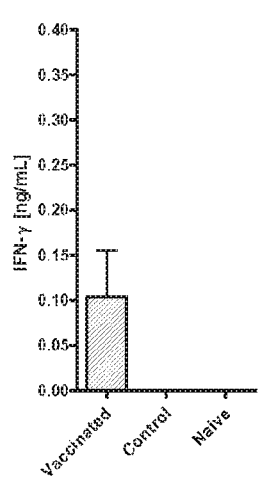
Fig. 19          Fig. 20

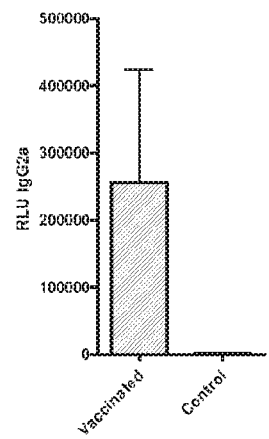 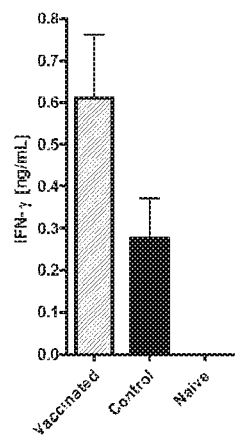 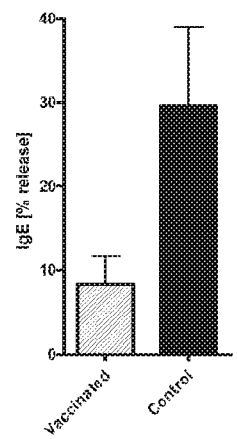
Fig. 21A Fig. 21B Fig. 21C
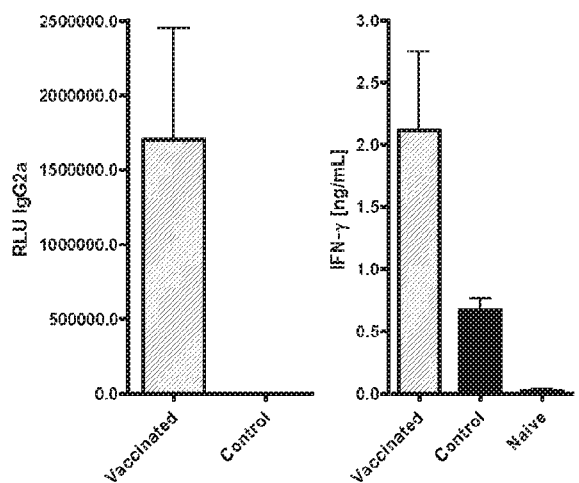 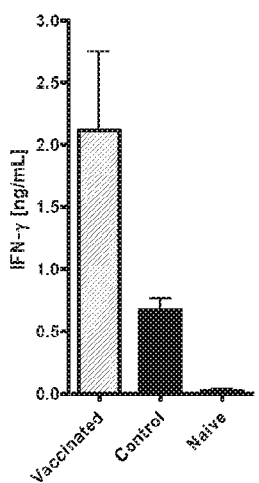
Fig. 22A Fig. 22B

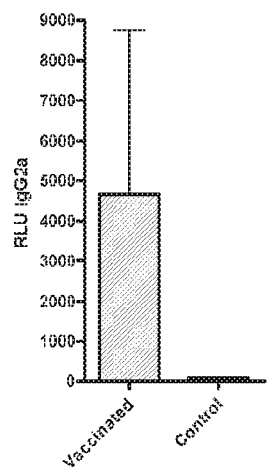 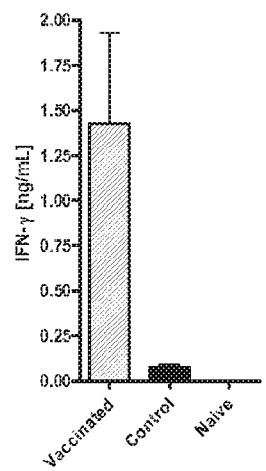 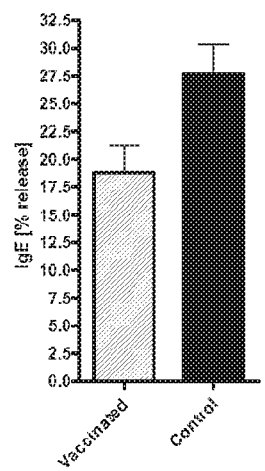
Fig. 23A        Fig. 23B        Fig. 23C
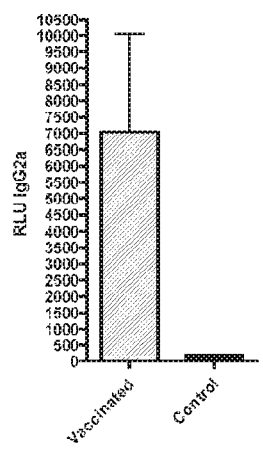 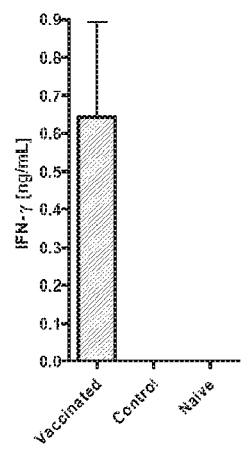 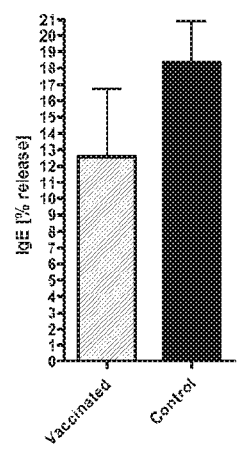
Fig. 24A        Fig. 24B        Fig. 24C

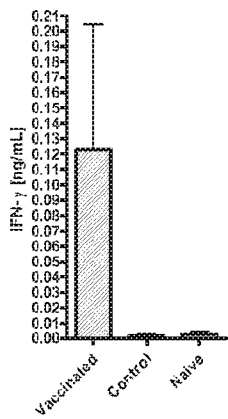
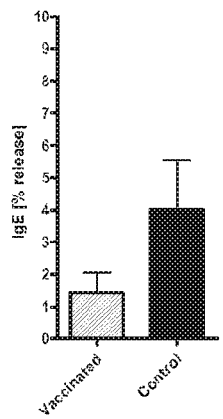
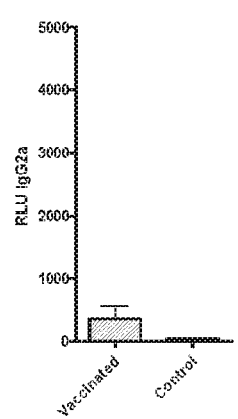
Fig. 25A　　　　Fig. 25B　　　　Fig. 26
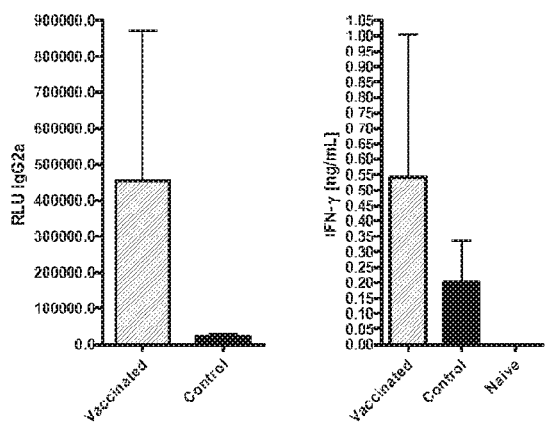
Fig. 27A　　　　Fig. 27B

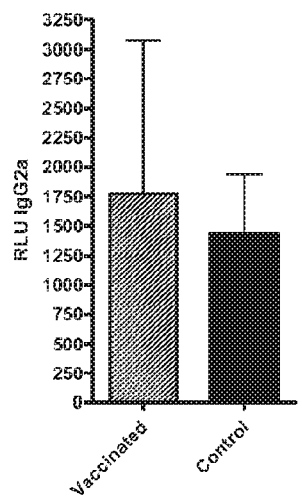
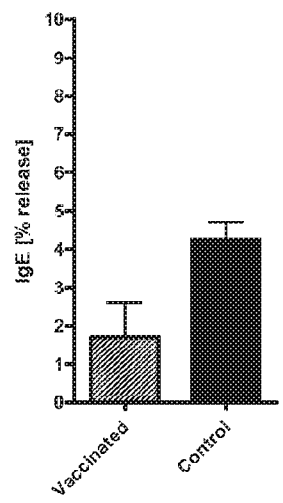
Fig. 28A        Fig. 28B
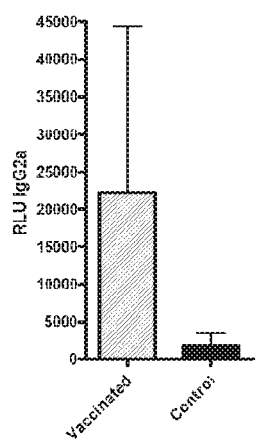
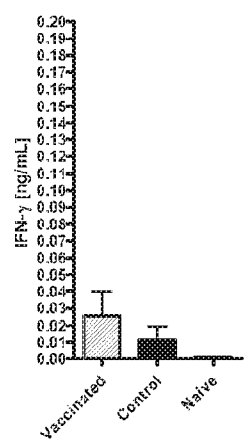
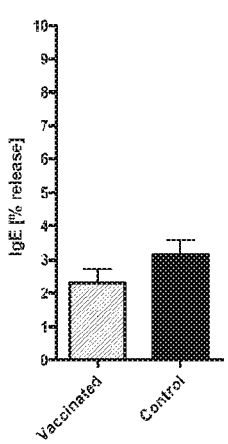
Fig. 29A        Fig. 29B        Fig. 29C

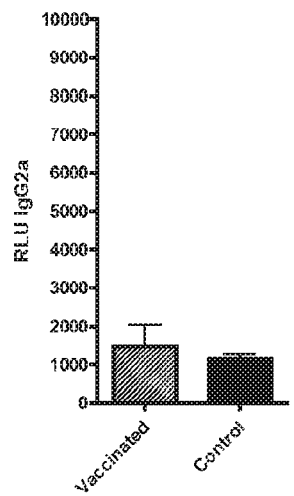 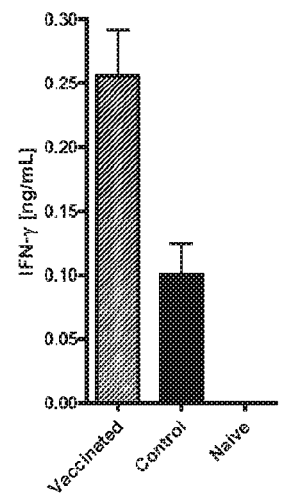
Fig. 34A  Fig. 34B
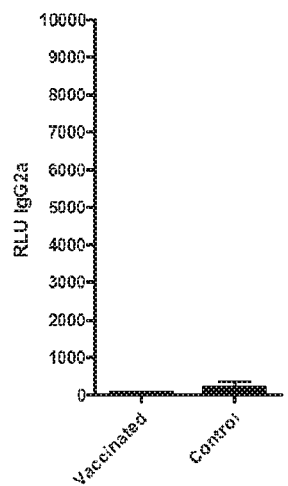 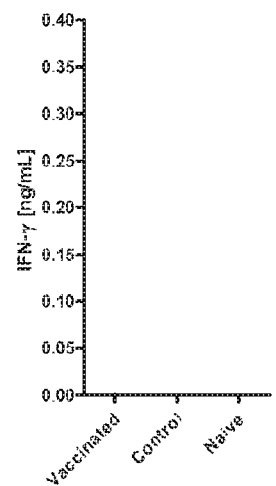
Fig. 35A  Fig. 35B

US 11,020,477 B2

RNA VACCINES

CROSS REFERENCE TO RELATED APPLICATIONS

This application is a divisional of U.S. application Ser. No. 14/026,436, filed on Sep. 13, 2013, which is a continuation of U.S. application Ser. No. 12/680,354, filed on Nov. 1, 2010, which is the U.S. national stage application of International Patent Application No. PCT/EP2008/063035, filed Sep. 29, 2008, the entire content of which is incorporated herein by reference.

DESCRIPTION

The present invention relates to RNA vaccines.

During the last decades, type I allergic diseases have emerged as a major public health problem in Western industrialised countries with about 25% of the population being affected by now.

In addition to family predisposition, conditions of growing up—including early childhood infections—and dietary habits, but also environmental factors such as passive smoking or exposure to air pollutants have been demonstrated to be of great relevance for the development of atopic diseases.

Specific immunotherapy, which is performed by injections of escalating doses of allergen(s) over years, currently represents the only available therapeutic intervention. However, due to the high doses administered, the risk of anaphylactic side effects is evident and the use of crude, barely characterised allergen extracts implies the possibility for sensitisation of the patient against previously unrecognised components.

Additionally, there is no preventive vaccination against type I allergy available, although prevention of young children with increased hereditary risk to develop allergic disease may be the most feasible approach. Training of the naive immune system is easier to accomplish than balancing an already manifested allergic immune phenotype.

In Ying et al. (Nature Med (1999) 5:823-827) self-replicating RNA vaccines are disclosed whose RNA encodes for β-galactosidase, which is often used as a model molecule for studying immunological processes. In Ying et al. the antitumour reaction was studied and the induction of CD8 positive cells was observed. However, CD4 positive cells which were not investigated in Ying et al. mediate in contrast to CD8 positive cells immunological protection against allergies and prevent a class switch towards IgE in B-cells.

Recently, nucleic acid based vaccines have become a promising approach to bias immune mechanisms underlying allergic diseases. It has been shown in numerous animal studies, that DNA vaccines can prevent from the induction of type I allergic responses and even reverse an already established allergic TH2 immune status (Weiss, R. et al. (2006) *Int Arch Allergy Immunol* 139:332-345).

Nevertheless, general concerns have been raised regarding the safety of DNA based vaccines: The introduced DNA molecules could potentially integrate into the host genome or, due to their distribution to various tissues, could lead to sustained delivery of allergen, thus inducing uncontrollable anaphylactic reactions within patients with pre-existing allergen-specific IgE molecules. Furthermore, vaccination of healthy children requires the highest safety standards for any anti-allergy vaccine.

BRIEF DESCRIPTION OF THE DRAWINGS

FIGS. 16A and 16B show the induction of Th 1 memory and suppression of IgE responses by RNA pTNT-Phlp 7.

FIGS. 17A, 17B, and 17C show the induction of Th 1 memory and suppression of IgE responses by RNA pTNT-hybrid (Phlp 1-2-5-6).

FIGS. 18A and 18B show the induction of Th 1 memory by RNA pTNT-Cry j 1.

FIG. 19 shows the induction of Th 1 memory by RNA pTNT-Jun a 1.

FIG. 20 shows the induction of Th 1 memory by RNA pTNT-Amb a 1.

FIGS. 21A, 21B, and 21C show the induction of Th 1 memory and suppression of IgE responses by RNA pTNT-Api g 1.

FIGS. 22A and 22B show the induction of Th 1 memory by RNA pTNT-Dau c 1.

FIGS. 23A, 23B, and 23C show the induction of Th 1 memory and suppression of IgE responses by RNA pTNT-Mal d 1.

FIGS. 24A, 24B, and 24C show the induction of Th 1 memory and suppression of IgE responses by RNA pTNT-Ova.

FIGS. 25A and 25B show the induction of Th 1 memory and suppression of IgE responses by RNA pTNT-Beta-Casein.

FIG. 26 shows the induction of Th 1 memory responses by RNA pTNT-Cyp c 1.

FIGS. 27A and 27B show the induction of Th 1 memory responses by RNA pTNT-Fel d 1.

FIGS. 28A and 28B show the induction of Th 1 memory and suppression of IgE responses by RNA pTNT-Der p 2.

FIGS. 29A, 29B, and 29C shows the induction of Th 1 memory and suppression of IgE responses by RNA pTNT-Alt a 1.

FIGS. 34A and 34B show the induction of Th 1 memory by RNA pTNT-Que a 1.

FIGS. 35A and 35B show no induction of Th 1 memory by RNA pTNT-Art v 1.

Figure 1:
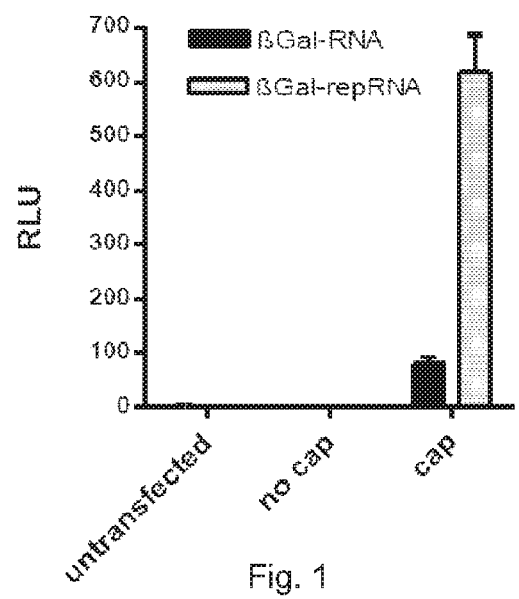
FIG. 1 shows in vitro transfection of BHK-21 cells with RNA (βGal-RNA) or self-replicating RNA (βGal-repRNA) transcripts encoding β-galactosidase.

It is therefore an object of the present invention to provide an allergen vaccine which overcomes the drawbacks of DNA vaccines and still allows for an effective treatment of allergies or successfully prevents from sensitisation against an allergen.

Therefore the present invention relates to an RNA vaccine comprising at least one RNA molecule encoding for at least one allergen or derivative thereof, wherein said allergen is an allergen of *Alnus glutinosa, Alternaria alternata, Ambrosia artemisiifolia, Apium graveolens, Arachis hypogaea, Betula verrucosa, Carpinus betulus, Castanea sativa, Cladosporium herbarum, Corylus avellana, Cryptomeria japonica, Cyprinus carpio, Daucus carota, Dermatophagoides pteronyssinus, Fagus sylvatica, Felis domesticus, Hevea brasiliensis, Juniperus ashei, Malus domestica, Quercus alba* and *Phleum pratense*.

It turned out that RNA molecules encoding an allergen or derivative thereof may also be used efficiently as RNA vaccines. RNA vaccines exhibit the features attributed to DNA vaccines for the treatment of allergic diseases: They provide the allergen in its purest form, i.e. its genetic information, and, similar to DNA vaccines, they induce TH1-biased immune reactions. Furthermore, similar methods as developed for DNA vaccines to create hypoallergenic gene products, can be implemented with RNA vaccines, as well.

Besides, RNA vaccines offer striking advantages over DNA vaccines: (i) The vaccine contains the pure genetic information of the allergen but no additional foreign sequences, such as viral promoters, antibiotic resistance genes, or viral/bacterial regulatory sequences that are usually present in the backbone of plasmids used for DNA vaccines. (ii) RNA cannot integrate into the host genome thus abolishing the risk of malignancies. (iii) RNA is translated in the cytoplasm of the cell, hence the transcription machinery of the cell nucleus is not required, rendering RNA vaccines independent of transport into and out of the nucleus as well as of nuclear stages. (iv) Due to the rapid degradation of RNA, expression of the foreign transgene is short-lived, avoiding uncontrollable long term expression of the antigen.

The RNA vaccine of the present invention may comprise more than one RNA molecule encoding an allergen, preferably two, three, five, ten, etc. However, one RNA molecule may also encode for at least one allergen, which means that one RNA molecule comprises a nucleotide sequence encoding for at least one, two, three, five, ten, etc. different or identical allergens. The allergens to be encoded by one or more RNA molecules may be selected from the list below in any combination.

As used herein, the term "RNA vaccine" refers to a vaccine comprising an RNA molecule as defined herein. Said vaccine may comprise, however, of course other substances and molecules which are required or which are advantageous when said vaccine is administered to an individual (e.g. pharmaceutical excipients).

The term "allergen of" is used interchangeable with the terms "allergen derived from" and "allergen obtained from". This means that the allergen is naturally expressed in said organisms and the DNA/RNA encoding said allergens is isolated in order to produce the RNA molecules of the present invention.

It turned out that not all RNA molecules encoding an allergen can induce the formation of allergen-specific antibodies when administered to a mammal or human being. RNA molecules encoding for Artemisia vulgaris allergen Art v 1 and Olea europea allergen Ole e 1, for instance, are not able to induce Th 1 memory and to suppress the allergen specific IgE response. However, RNA molecules encoding the allergen of the above mentioned sources are capable to do so.

According to a preferred embodiment of the present invention the allergen of *Alnus glutinosa* is Aln g 1, the allergen of *Alternaria alternata* is selected from the group consisting of Alt a 1, Alt a 3, Alt a 4, Alt a 5, Alt a 6, Alt a 7, Alt a 8, Alt a 10, Alt a 12 and Alt a 13, the allergen of *Ambrosia artemisiifolia* is selected from the group consisting of Amb a 1, Amb a 2, Amb a 3, Amb a 5, Amb a 6, Amb a 7, Amb a 8, Amb a 9 and Amb a 10, the allergen of *Apium graveolens* is selected from the group consisting of Api g 1, Api g 4 and Api g 5, the allergen of *Arachis hypogaea* is selected from the group consisting of Ara h 1, Ara h 2, Ara h 3, Ara h 4, Ara h 5, Ara h 6, Ara h 7 and Ara h 8, the allergen of *Betula verrucosa* is selected from the group consisting of Bet v 1, Bet v 2, Bet v 3, Bet v 4, Bet v 6 and Bet v 7, the allergen of *Carpinus betulus* is Car b 1, the allergen of *Castanea sativa* is selected from the group consisting of Cas s 1, Cas s 5 and Cas s 8, the allergen of *Cladosporium herbarum* is selected from the group consisting of Cla h 2, Cla h 5, Cla h 6, Cla h 7, Cla h 8, Cla h 9, Cla h 10 and Cla h 12, the allergen of *Corylus avellana* is selected from the group consisting of Cor a 1, Cora 2, Cora 8, Cora 9, Cora 10 and Cora 11, the allergen of *Cryptomeria japonica* is selected from the group consisting of Cry j 1 and Cry j 2, the allergen of *Cyprinus carpio* is Cyp c 1, the allergen of *Daucus carota* is selected from the group consisting of Dau c 1 and Dau c 4, the allergen of *Dermatophagoides pteronyssinus* is selected from the group consisting of Der p 1, Der p 2, Der p 3, Der p 4, Der p 5, Der p 6, Der p 7, Der p 8, Der p 9, Der p 10, Der p 11, Der p 14, Der p 20, Der p 21 and Clone 30 allergen, the allergen of *Fagus sylvatica* is Fag s 1, the allergen of *Felis domesticus* is selected from the group consisting of Fel d 1, Fel d 2, Fel d 3, Fel d 4, Fel d 5w, Fel d 6w and Fel d 7w, the allergen of *Hevea brasiliensis* is selected from the group consisting of Hey b 1, Hey b 2, Hey b 3, Hey b 4, Hey b 5, Hey b 6.01, Hey b 6.02, Hey b 6.03, Hey b 7.01, Hey b 7.02, Hey b 8, Hey b 9, Hey b 10, Hey b 11, Hey b 12 and Hey b 13, the allergen of *Juniperus ashei* is selected from the group consisting of Jun a 1, Jun a 2 and Jun a 3, the allergen of *Malus domestica* is selected from the group consisting of Mal d 1, Mal d 2, Mal d 3 and Mal d 4, the allergen of *Quercus alba* is Que a 1 and the allergen of *Phleum pratense* is selected from the group consisting of Phlp 1, Phlp 2, Phlp 4, Phlp 5, Phlp 6, Phlp 7, Phlp 11, Phlp 12 and Phlp 13.

According to a preferred embodiment of the present invention the allergen is selected from the group consisting of:

| | |
|---|---|
| Grass Pollen: | Phl p 1, Phl p 2, Phl p 5, Phl p 6, Phl p 7, Phl p 12 |
| House Dust Mite: | Der p 1, Der p 2, Der p 7, Der p 21, Clone 30 allergen (PCT- application AT2007/000201, Austrian patent application AT 503530: MKFNIIVFI SLAILVHSSY AANDNDDDPT TTVHPTTTEQ PDDKFECPSR FGYFADPKDP HKFYICSNWE AVHKDCPGNT RWNEDEETCT, SEQ ID No. 1) |
| Birch Pollen: | Bet v 1 and its homologous tree (Aln g 1, Cor a 1, Fag s 1) or food allergens) Mal d 1, Api g 1, Pru p 1) |
| Cat: | Fel d 1, Fel d 2 |
| Weeds (Ragweed, Mugwort): | Amb a 1 |
| Cypress/Juniper/ Cedar: | Cry j 1, Cry j 2, Jun a 1, Jun a 3, Cha o 1, Cha o 2, Cup a 1, Cup a 3, Jun a 1, Jun a 3, Pla a 3 |
| Peanut: | Ara h 1, Ara h 2, Ara h 4 |
| Hazelnut: | Cor a 8, Cor a 9 |
| Fish/Shrimps: | Gad c 1, Cyp c 1, Pen a 1 |

Especially preferred allergens to be used in an RNA vaccine of the present invention are selected from the group consisting of Aln g 1, Alt a 1, Amb a 1, Api g 1, Ara h 2, Bet v 1, beta-casein, Car b 1, Cas s 1, Cla h 8, Cora 1, Cry j 1, Cyp c 1, Dau c 1, Der p 2, Fags 1, Fel d 1, Hev b 6, Jun a 1, Mal d 1, ovalbumin (OVA), Phlp 1, Phlp 2, Phlp 5, Phlp 6 and Phlp 7.

It turned out that the above identified allergens are particularly suited to be used in RNA vaccines. However, it is of course also possible to use the present invention for other allergens, such as Amb a 1, Amb a 2, Amb a 3, Amb a 5, Amb a 6, Amb a 7, Amb a 8, Amb a 9, Amb a 10, Amb t 5, Hel a 1, Hel a 2, Hel a 3, Mer a 1, Che a 1, Che a 2, Che a 3, Sal k 1, Cat r 1, Pla l 1, Hum j 1, Par j 1, Par j 2, Par j 3, Par o 1, Cyn d 1, Cyn d 7, Cyn d 12, Cyn d 15, Cyn d 22w, Cyn d 23, Cyn d 24, Dac g 1, Dac g 2, Dac g 3, Dac g 5, Fes p 4w, Hol l 1, Lol p 1, Lol p 2, Lol p 3, Lol p 5, Lol p 11, Pha a 1, Phlp 1, Phlp 2, Phlp 4, Phlp 5, Phlp 6, Phlp 11, Phlp 12, Phlp 13, Poa p 1, Poa p 5, Sor h 1, Pho d 2, Aln g 1, Bet v 1, Bet v 2, Bet v 3, Bet v 4, Bet v 6, Bet v 7, Car b 1, Cas s 1, Cas s 5, Cas s 8, Cor a 1, Cor a 2, Cor a 8, Cor a 9, Cora 10, Cora 11, Que a 1, Fra e 1, Lig v 1, Syr v 1, Cry j 1, Cry j 2, Cup a 1, Cups 1, Cup s 3w, Jun a 1, Jun a 2, Jun a 3, Jun o 4, Jun s 1, Jun v 1, Pla a 1, Pla a 2, Pla a 3, Aca s 13, Blot 1, Blot 3, Blot 4, Blot 5, Blot 6, Blot 10, Blot 11, Blot 12, Blot 13, Blot 19, Der f 1, Der f 2, Der f 3, Der f 7, Der f 10, Der f 11, Der f 14, Der f 15, Der f 16, Der f 17, Der f 18w, Der m 1, Der p 1, Der p 2, Der p 3, Der p 4, Der p 5, Der p 6, Der p 7, Der p 8, Der p 9, Der p 10, Der p 11, Der p 14, Der p 20, Der p 21, Eur m 2, Eur m 14, Gly d 2,Lep d 1, Lep d 2, Lep d 5, Lep d 7, Lep d 10, Lep d 13, Tyr p 2, Tyr p 13, Bos d 2, Bos d 3, Bos d 4, Bos d 5, Bos d 6, Bos d 7, Bos d 8, Can f 1, Can f 2, Can f 3, Can f 4, Equ c 1, Equ c 2, Equ c 3, Equ c 4, Equ c 5, Fel d 1, Fel d 2, Fel d 3, Fel d 4, Fel d 5w, Fel d 6w, Fel d 7w, Cav p 1, Cav p 2, Mus m 1, Rat n 1, Alta 1, Alta 3, Alta 4, Alta 5, Alta 6, Alta 7, Alta 8, Alta 10, Alt a 12, Alt a 13, Cla h 2, Cla h 5, Cla h 6, Cla h 7, Cla h 8, Cla h 9, Cla h 10, Cla h 12, Asp fl 13, Asp f 1, Asp f 2, Asp f 3, Asp f 4, Asp f 5, Asp f 6, Asp f 7, Asp f 8, Asp f 9, Asp f 10, Asp f 11, Asp f 12, Asp f 13, Asp f 15, Asp f 16, Asp f 17, Asp f 18, Asp f 22w, Asp f 23, Asp f 27, Asp f 28, Asp f 29, Asp n 14, Asp n 18, Asp n 25, Asp o 13, Asp o 21, Pen b 13, Pen b 26, Pen ch 13, Pen ch 18, Pen ch 20, Pen c 3, Pen c 13, Pen c 19, Pen c 22w, Pen c 24, Pen o 18, Fus c 1, Fus c 2, Tri r 2, Tri r 4, Tri t 1, Tri t 4, Cand a 1, Cand a 3, Cand b 2, Psi c 1, Psi c 2, Cop c 1, Cop c 2, Cop c 3, Cop c 5, Cop c 7, Rho m 1, Rho m 2, Mala f 2, Mala f 3, Mala f 4, Malas 1, Malas 5, Malas 6, Malas 7, Malas 8, Malas 9, Malas 10, Malas 11, Mala s 12, Mala s 13, Epi p 1, Aed a 1, Aed a 2, Api m 1, Api m 2, Api m 4, Api m 6, Api m 7, Born p 1,Bom p 4, Bla g 1, Bla g 2, Bla g 4, Bla g 5, Bla g 6, Bla g 7, Bla g 8, Per a 1, Per a 3, Per a 6, Per a 7, Chi k 10, Chi t 1-9, Chi t 1.01, Chi t 1.02, Chi t 2.0101, Chi t 2.0102, Chi t 3, Chit 4, Chit 5, Chit 6.01, Chit 6.02, Chit 7, Chit 8, Chit 9, Cte f 1, Cte f 2, Cte f 3, Tha p 1, Lep s 1, Dol m 1, Dol m 2, Dol m 5, Dol a 5, Pol a 1, Pol a 2, Pol a 5, Pol d 1, Pol d 4, Pol d 5, Pol e 1, Pol e 5, Pol f 5, Pol g 5, Pol m 5, Vesp c 1, Vesp c 5, Vesp m 1, Vesp m 5, Ves f 5, Ves g 5, Ves m 1, Ves m 2, Ves m 5, Ves p 5, Ves s 5, Ves vi 5, Ves v 1, Ves v 2, Ves v 5, Myr p 1, Myr p 2, Sol g 2, Sol g 4, Soli 2, Soli 3, Soli 4, Sols 2, Tria p 1, Gad c 1, Sal s 1, Bos d 4, Bos d 5, Bos d 6, Bos d 7, Bos d 8, Gal d 1, Gal d 2, Gal d 3, Gal d 4, Gal d 5, Mete 1, Pen a 1, Pen i 1, Pen m 1, Pen m 2, Tod p 1, Hel as 1, Hal m 1, Ran e 1, Ran e 2, Bra j 1, Bran 1, Bra o 3, Bra r 1, Bra r 2, Hor v 15, Hor v 16, Hor v 17, Hor v 21, Sec c 20, Tri a 18, Tri a 19, Tri a 25, Tri a 26, Zea m 14, Zea m 25, Ory s 1, Api g 1, Api g 4, Api g 5, Dau c 1, Dau c 4, Cor a 1.04, Cor a 2, Cor a 8, Fra a 3, Fra a 4, Mal d 1, Mal d 2, Mal d 3, Mal d 4, Pyr c 1, Pyr c 4, Pyr c 5, Pers a 1, Pru ar 1, Pru ar 3, Pru av 1, Pru av 2, Pru av 3, Pru av 4, Pm d 3, Pm du 4, Pm p 3, Pm p 4, Aspa o 1, Cro s 1, Cro s 2, Lac s 1, Vit v 1, Mus xp 1, Ana c 1, Ana c 2, Cit 13, Cit s 1, Cit s 2, Cit s 3, Lit c 1, Sin a 1, Gly m 1, Gly m 2, Gly m 3, Gly m 4, Vig r 1, Ara h 1, Ara h 2, Ara h 3, Ara h 4, Ara h 5, Ara h 6, Ara h 7, Ara h 8, Len c 1, Len c 2, Pis s 1, Pis s 2, Act c 1, Act c 2, Cap a lw, Cap a 2, Lyc e 1, Lyc e 2, Lyc e 3, Sola t 1, Sola t 2, Sola t 3, Sola t 4, Ber e 1, Ber e 2, Jug n 1, Jug n 2, Jug r 1, Jug r 2, Jug r 3, Ana o 1, Ana o 2, Ana o 3, Ric c 1, Ses i 1, Ses i 2, Ses i 3, Ses i 4, Ses i 5, Ses i 6, Cuc m 1, Cuc m 2, Cuc m 3, Ziz m 1, Ani s 1, Ani s 2, Ani s 3, Ani s 4, Arg r, Asc s 1, Carp 1, Den n 1, Hev b 1, Hev b 2, Hev b 3, Hev b 4, Hev b 5, Hev b 6.01, Hev b 6.02, Hev b 6.03, Hev b 7.01, Hev b 7.02, Hev b 8, Hev b 9, Hev b 10, Hev b 11, Hev b 12, Hev b 13, Homs 1, Horn s2, Horns 3, Horns 4, Horn s 5 and Trips 1.

According to a preferred embodiment of the present invention the allergen derivative is hypoallergenic.

In order to induce a specific immune response in a mammal, in particular in a human, without provoking an allergenic reaction or by provoking a significantly reduced allergenic reaction, it is preferred that the allergen or derivative thereof exhibits hypoallergenic properties, i.e. the hypoallergenic molecule shows no or significantly reduced IgE reactivity.

As used herein, the term "hypoallergenic" refers to the ability of a peptide, polypeptide or protein derived from an allergen with allergenic properties to induce the induction of T cells specific for said allergen and exhibiting reduced or no allergic reactions when administered to an individual. The reduced or missing ability of "hypoallergenic" derivatives of an allergen to induce an allergic reaction in an individual is obtained by removing or destroying the IgE binding epitopes from said allergens, however, by conserving the T cell epitopes present on said allergens. This can be achieved, for instance, by splitting the allergen into fragments with reduced or no IgE binding capacity and optionally fusing some or all of said fragments in an order together which does not correspond to the order of the fragments in the wild-type allergen (see e.g. EP 1 440 979). Another method for producing "hypoallergenic" molecules from allergens involves C- and/or N-terminal deletions of the wild-type allergen (see e.g. EP 1 224 215). Of course it is also possible to generate hypoallergenic molecules by introducing specific mutations affecting one or more amino acid residues of the wild-type allergen, whereby said modifications result in a loss of the three-dimensional structure.

RNA vaccines are rendered hypoallergenic by targeting the resulting protein into the ubiquitination pathway of the cell, where the respective protein is degraded into hypoallergenic peptides. This is achieved by fusing the sequence encoding ubiquitin to the 5' end of the allergen encoding RNA. Ubiquitination efficacy can be enhanced by mutating amino acid residue 76 from glycine to alanine (G76.fwdarw.A76). Ubiquitination efficacy can be further enhanced by mutating the first amino acid of the allergen (methionine) to a destabilizing amino acid (Arginine) (M77.fwdarw.R77). Alternatively, ubiquitination of the resulting gene product can be achieved by adding a carboxyterminal destabilizing sequence known as PEST sequence.

According to a preferred embodiment of the present invention the hypoallergenic allergen derivative encoded by the RNA in the vaccine exhibits an IgE reactivity which is at least 10%, preferably at least 20%, more preferably at least 30%, in particular at least 50%, lower than the IgE reactivity of the wild-type allergen.

Hypoallergenicity of RNA vaccines can be routinely tested by translating the RNA in vitro in a rabbit reticulocyte lysate system. The resulting gene product will be analyzed by IgE western blots using pools of appropriate patients' sera. Reduction of IgE binding capacity of the respective hypoallergen will be assessed compared to the IgE binding capacity of the wild-type molecule, translated in said reticulocyte lysate system.

According to a particularly preferred embodiment of the present invention the RNA molecule of the invention may encode for more than one, preferably more than two, more preferably more than three, even more preferably more than four, allergens or derivatives thereof. In particular, the RNA molecule may encode for Phlp 1, Phlp 2, Phlp 5 and Phlp6, or for Aln g 1, Cora 1, Que a 1, Car b 1 and Bet v 1.

The RNA molecule encoding the allergen or derivative thereof is fused to at least one further peptide, polypeptide or protein.

The allergen encoding RNA sequence can by fused to RNA sequences encoding peptides, polypeptides, or proteins. These peptides can be signal peptides that target the allergen into the endoplasmic reticulum and thereby enhance protein secretion from the cell, for example the human tissue plasminogen activator signal peptide (hTPA). Said peptide or protein can be the lysosome-associated membrane protein (LAMP) or the 20-amino acid C-terminal tail of the lysosomal integral membrane protein-II (LIMP-II). The LAMP/LIMP-II sequences are used to direct the antigen protein to the major histocompatibility class II (MHC II) vesicular compartment of transfected professional antigen-presenting cells (APCs) thereby enhancing activation of T helper cells which increases vaccine efficacy. Said proteins or polypeptides can also be proteins that enhance the TH1 bias of the vaccine, e.g. the heat shock protein 70 (HSP70), or bacterial toxins like cholera toxin (CT) or related toxins such as heat labile enterotoxin (LT) of Escherichia coli.

According to a preferred embodiment of the present invention the RNA molecule comprises at least one further element selected from the group consisting of replicase, β-globin leader sequence, cap0, cap1 and poly A tail.

The RNA vaccine consists of the RNA sequence encoding the respective allergen. This RNA sequence can be the wild-type sequence of the allergen or can be adapted with respect to its codon usage. Adaption of codon usage can increase translation efficacy and half-life of the RNA. A poly A tail consisting of at least 30 adenosine residues is attached to the 3' end of the RNA to increase the half-life of the RNA. The 5' end of the RNA is capped with a modified ribonucleotide with the structure m7G(5')ppp(5')N (cap 0 structure) or a derivative thereof which can be incorporated during RNA synthesis or can be enzymatically engineered after RNA transcription by using Vaccinia Virus Capping Enzyme (VCE, consisting of mRNA triphosphatase, guanylyl-transferase and guanine-7-methytransferase), which catalyzes the construction of N7-monomethylated cap 0 structures. Cap 0 structure plays a crucial role in maintaining the stability and translational efficacy of the RNA vaccine. The 5' cap of the RNA vaccine can be further modified by a 2'-O-Methyltransferase which results in the generation of a cap 1 structure (m7Gppp[m2'-O]N), which further increases translation efficacy.

RNA vaccines can be further optimised by converting them into self-replicating vaccines. Such vectors include replication elements derived from alphaviruses and the substitution of the structural virus proteins with the gene of interest. Replicase-based RNA vaccines have been demonstrated to induce antibody as well as cytotoxic responses at extremely low doses due to immune activation mediated by virus-derived danger signals (Ying, H. et al. (1999) Nat Med 5:823-827).

The RNA vaccine can also be a self-replicating RNA vaccine. Self-replicating RNA vaccines consisting of a replicase RNA molecule derived from semliki forest virus (SFV), sindbis virus (SIN), venezuelan equine encephalitis virus (VEE), Ross-River virus (RRV), or other viruses belonging to the alphavirus family. Downstream of the replicase lies a subgenomic promoter that controls replication of the allergen RNA followed by an artificial poly A tail consisting of at least 30 adenosine residues.

According to another preferred embodiment of the present invention the vaccine comprises further CpG-DNA and cytokines, preferably interleukin (IL)-12 and IL-15.

The vaccine or vaccine formulation according to the present invention can further include an adjuvant. "Adjuvant", according to the present invention, refers to a compound or mixture that enhances the immune response to an antigen. An adjuvant may also serve as a tissue depot that slowly releases the antigen. Adjuvants include among others complete Freund's adjuvant, incomplete Freund's adjuvant, saponin, mineral gels such as aluminum hydroxide, surface active substances such as lysolecithin, pluronic polyols, polyanions, peptides, Levamisol, CpG-DNA, oil or hydrocarbon emulsions, and potentially useful adjuvants such as BCG (bacille Calmette-Guerin) and Corynebacterium parvum.

Alternatively, or in addition, also immunostimulatory proteins can be provided as an adjuvant or to increase the immune response to a vaccine. Vaccination effectiveness may be enhanced by co-administration of an immunostimulatory molecule (Salgaller and Lodge, J. Surg. Oncol. (1988) 68:122), such as an immunostimulatory, immunopotentiating or pro-inflammatory cytokine, lymphokine, or chemokine with the vaccine, particularly with a vector vaccine. For example, cytokines or cytokine genes such as IL-2, IL-3, IL-12, IL-15, IL-18, IFN-gamma, IL-10, TGF-beta, granulocyte-macrophage (GM)-colony stimulating factor (CSF) and other colony stimulating factors, macrophage inflammatory factor, Flt3 ligand (Lyman, Curr. Opin. Hematol., 1998, 5:192), CD40 ligand, as well as some key costimulatory molecules or their genes (e.g., B7.1, B7.2) can be used. These immunostimulatory molecules can be delivered systemically or locally as proteins or be encoded by the RNA molecule or a further RNA molecule in the RNA vaccine of the present invention. As immunostimulatory molecules also polycationic peptides such as polyarginine may be employed.

According to a further preferred embodiment of the present invention the vaccine is adapted for intramuscular, intradermal, intravenous, transdermal, topical, or biolistic administration.

The RNA vaccine of the present invention may be administered in various ways. One way, for instance, is to transfer in vivo the RNA vaccine directly into a body (e.g. intramuscular, intradermal, intravenous, intranasal etc.). Alternatively it is possible to place RNA into cells (e.g. epidermal cells) outside of the body, e.g. epidermal cells are transfected with the RNA vaccine in vitro and then administered (transplanted) to a body. The cells can be transfected by exogenous or heterologous RNA when such RNA has been introduced inside the cell. The RNA can be introduced into the cells by pulsing, i.e. incubating the cells with the RNA molecules of the invention. Alternatively, the RNA can be introduced in vivo by lipofection, as naked RNA, or with other transfection facilitating agents (peptides, polymers, etc.). Synthetic cationic lipids can be used to prepare liposomes for in vivo transfection. Useful lipid compounds and compositions for transfer of nucleic acids are, e.g. DODC, DOPE, CHOL, DMEDA, DDAB, DODAC, DOTAP and DOTMA. Other molecules are also useful for facilitating transfection of a nucleic acid in vivo, such as cationic oligopeptides (e.g. WO 95/21931), peptides derived from DNA binding proteins (e.g. WO96/25508), or cationic polymers (e.g. WO 95/21931). Also polyethylenimine and its derivatives, polylactide-polyglycolide, and chitosan may be used. Alternatively, RNA molecules can be introduced into the desired host cells by methods known in the art, e.g. electroporation, microinjection, cell fusion, DEAE dextran, calcium phosphate precipitation, or use of a gene gun (biolistic transfection, see e.g. Tang et al., Nature (1992) 356: 152-154).

Another aspect of the present invention relates to the use of at least one RNA molecule as defined herein for the manufacture of a vaccine for treating or preventing allergy.

A further aspect of the present invention relates to the use of at least one RNA molecule as defined herein for the manufacture of a vaccine for hyposensitising an individual to an allergen.

According to another preferred embodiment of the present invention the vaccine is adapted for intramuscular, intradermal, intravenous, transdermal, topical or biolistic administration.

Another aspect of the present invention relates to an isolated RNA molecule comprising at least one nucleotide sequence encoding at least one allergen or derivative thereof. Said RNA molecule preferably comprises at least one nucleotide sequence selected from the group consisting of cap0, cap1, 5' β-globin leader sequence, self-replicating RNA, recoded allergen sequence and artificial poly-A tail, whereby Cap0—allergen sequence—poly A tail is an especially preferred RNA molecule. Cap0 is useful for the in vivo production of antibodies and with respect to self-replicating RNA vaccines for the induction of allergen specific T cells and IFN-gamma secretion.

The present invention is further illustrated by the following figures and examples without being restricted thereto.

FIG. 1 shows in vitro transfection of BHK-21 cells with RNA ((βGal-RNA) or self-replicating RNA ((βGal-repRNA) transcripts encoding (β-galactosidase. RNA transcripts with (cap) or without (no cap) addition of a m7G(5') ppp(5')G cap structure were tested. Untransfected cells served as background control (untransfected). Data are shown as means±SEM of three independent transfection experiments.

Figure 2A:
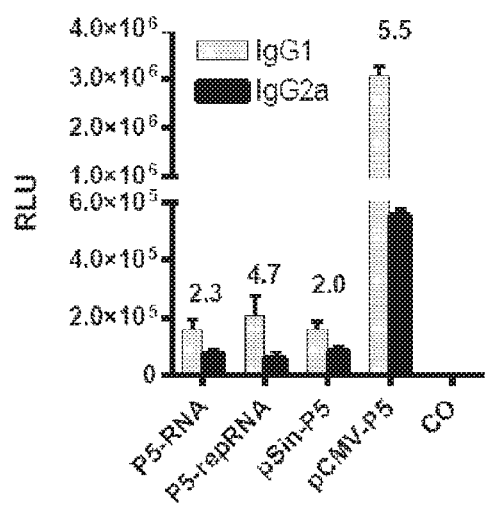
FIG. 2A shows Phlp 5 specific IgG1 and IgG2a levels after nucleic acid vaccination.
Figure 2B:
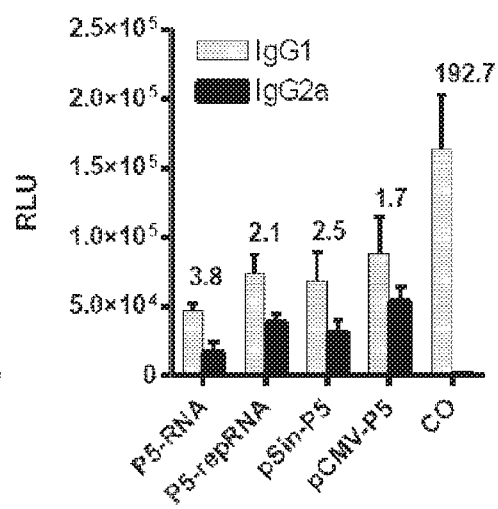
FIG. 2B shows Phlp 5 specific IgG1 and IgG2a levels after subsequent sensitisation with recombinant allergen in alum.

FIGS. 2A and 2B show Phlp 5 specific IgG1 and IgG2a levels after nucleic acid vaccination (FIG. 2A) and subsequent sensitisation with recombinant allergen in alum (B). Sera were diluted 1:1000 (A) and 1:100000 (FIG. 2B). Numbers on top of bars represent average IgG1:IgG2a ratios for the respective group. Data are shown as means±SEM (n=4).

Figure 3:
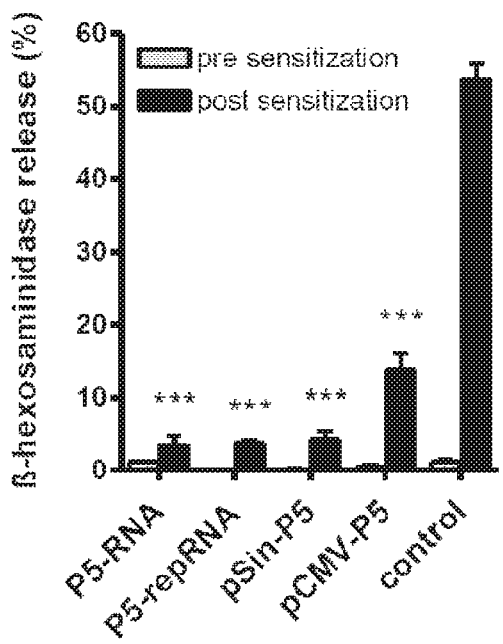
FIG. 3 shows Phlp 5 specific IgE measured via RBL release assay.

FIG. 3 shows Phlp 5 specific IgE measured via RBL release assay. IgE levels were measured after vaccination with the respective nucleic acid vaccines (grey bars) and after subsequent sensitisation with recombinant allergen in alum (black bars). Values are shown as means of % specific hexosaminidase release±SEM (n=4). ***: P<0.001.

Figure 4A:
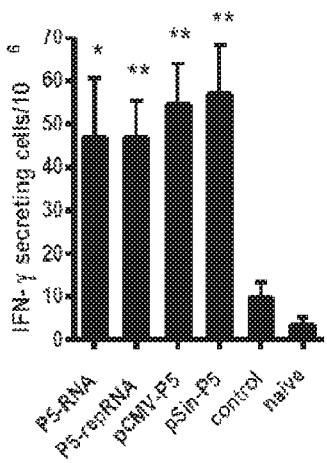
FIG. 4A shows the number of IFN-gamma secreting splenocytes after in vitro re-stimulation with recombinant Phlp 5 as determined by ELISPOT.
Figure 4B:
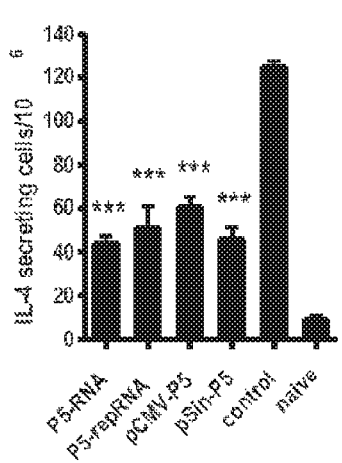
FIG. 4B shows the number of IL-4 secreting splenocytes after in vitro re-stimulation with recombinant Phlp 5 as determined by ELISPOT.
Figure 4C:
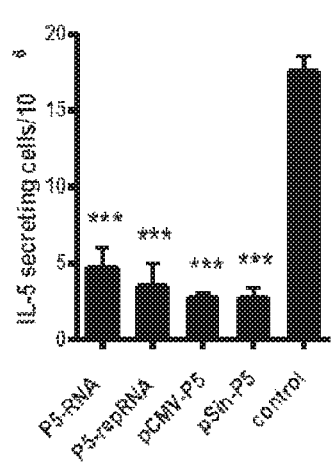
FIG. 4C shows the number of IL-5 secreting splenocytes after in vitro re-stimulation with recombinant Phlp 5 as determined by ELISPOT.

FIGS. 4A and 4B show the number of IFN-gamma (FIG. 4A), IL-4 (FIG. 4B), and IL-5 (FIG. 4C) secreting splenocytes after in vitro re-stimulation with recombinant Phlp 5 as determined by ELISPOT. Data are shown as means±SEM (n=4) of numbers of cytokine secreting cells per $10^6$ splenocytes.

Figure 5A:
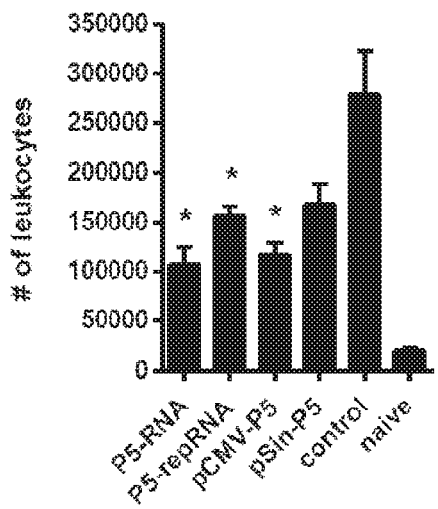
FIG. 5A shows the number of total leukocyte in BALF of sensitised mice after i.n. application of allergen.
Figure 5B:
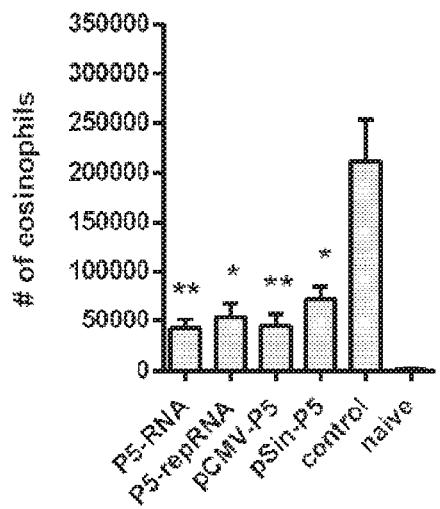
FIG. 5B shows the number of total eosinophils in BALF of sensitised mice after i.n. application of allergen.

FIGS. 5A and 5B show the number of total leukocytes (FIG. 5A) and eosinophils (FIG. 5B) in BALF of sensitised mice after i.n. application of allergen. Values are shown as means±SEM (n=4). *: P<0.05; **:P<0.01.

Figure 6A:
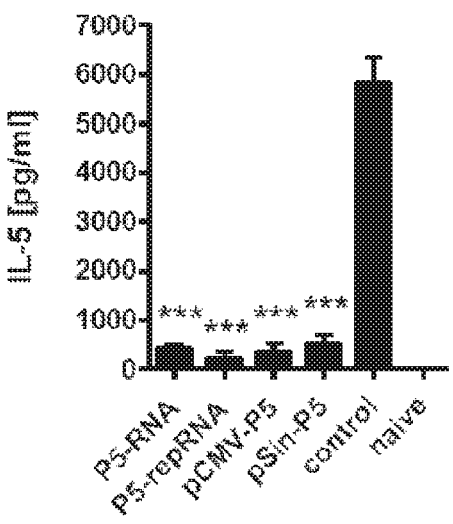
FIG. 6A shows the levels of IL-5 in BALF of sensitised mice after i.n. application of allergen.
Figure 6B:
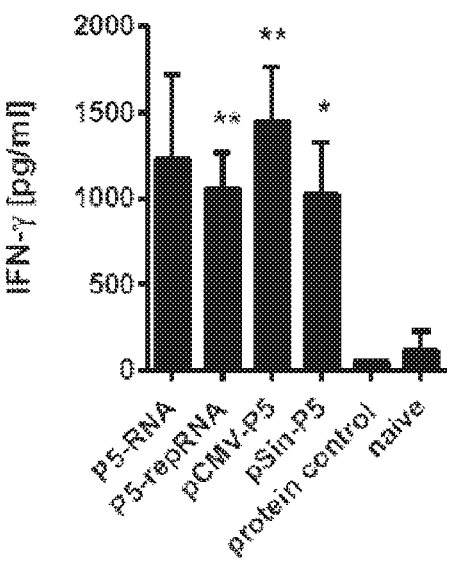
FIG. 6B shows the levels of IFN-γ in BALF of sensitised mice after i.n. application of allergen.

FIGS. 6A and 6B show the levels of IL-5 (FIG. 6A) and IFN-γ (FIG. 6B) in BALF of sensitised mice after i.n. application of allergen. Values are shown as means±SEM (n=4). *: P<0.05; :P<0.01; *:P<0.001.

Figure 7A:
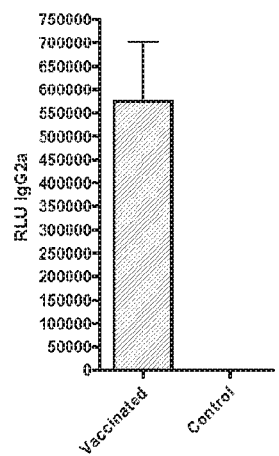
FIGS. 7A, 7B, and 7C show the induction of Th 1 memory and suppression of IgE responses by RNA pTNT-Bet v 1.
Figure 7B:
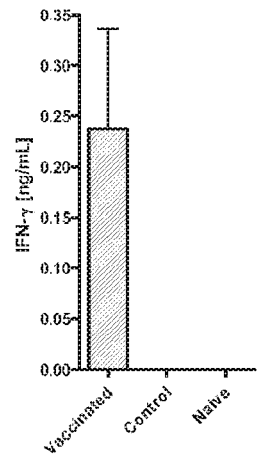
Figure 7C:
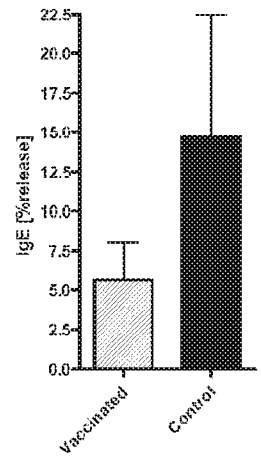

FIGS. 7A, 7B, and 7C show the induction of Th 1 memory and suppression of IgE responses by RNA pTNT-Bet v 1.

Figure 8A:
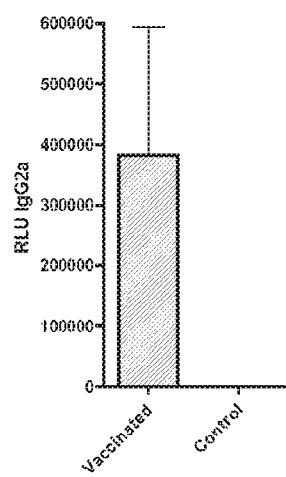
FIGS. 8A, 8B, and 8C show the induction of Th 1 memory and suppression of IgE responses by RNA pTNT-Car b 1.
Figure 8B:
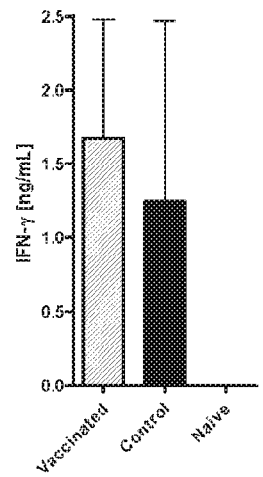
Figure 8C:
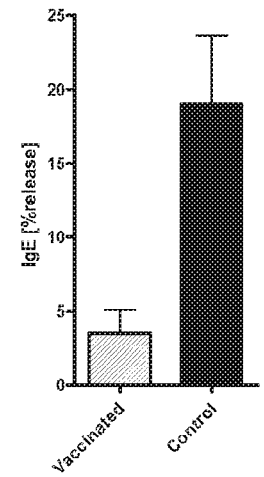

FIGS. 8A, 8B, and 8C show the induction of Th 1 memory and suppression of IgE responses by RNA pTNT-Car b 1.

Figure 9A:
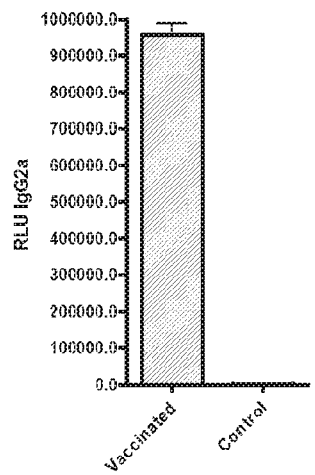
FIGS. 9A, 9B, and 9C show the induction of Th 1 memory and suppression of IgE responses by RNA pTNT-Cas s 1.
Figure 9B:
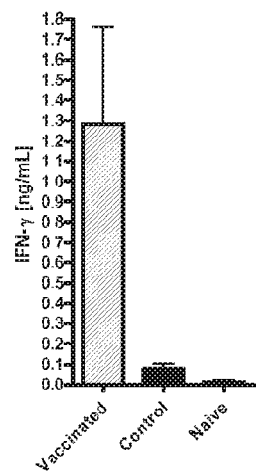
Figure 9C:
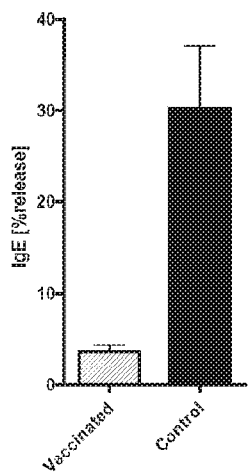

FIGS. 9A, 9B, and 9C show the induction of Th 1 memory and suppression of IgE responses by RNA pTNT-Cas s 1.

Figure 10A:
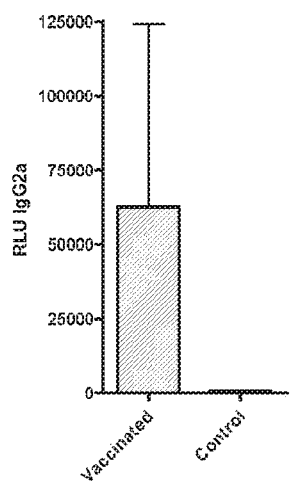
FIGS 10A and 10B show the induction of Th 1 memory by RNA pTNT-Phlp 1.
Figure 10B:
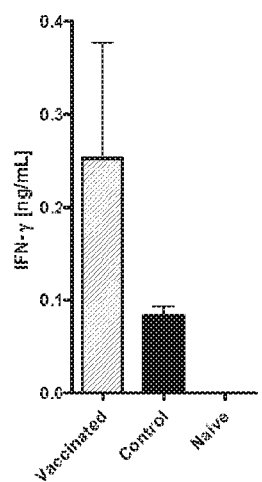

FIGS. 10A and 10B show the induction of Th 1 memory by RNA pTNT-Phlp 1.

Figure 11A:
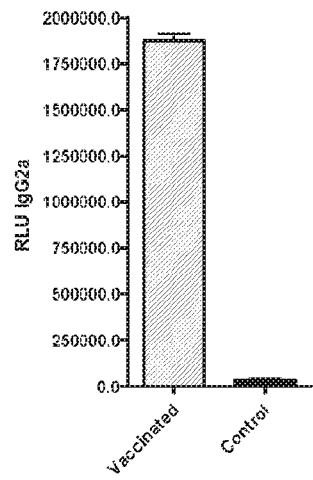
FIGS. 11A, 11B, and 11C show the induction of Th 1 memory and suppression of IgE responses by RNA pTNT-Phlp 6.
Figure 11B:
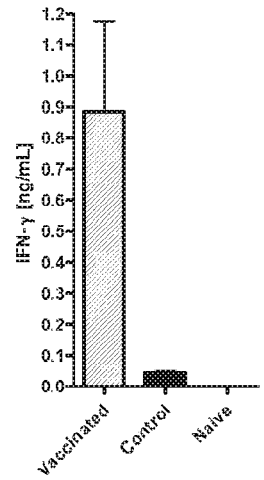
Figure 11C:
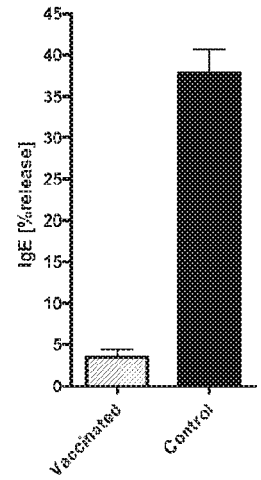

FIGS. 11A, 11B, and 11C show the induction of Th 1 memory and suppression of IgE responses by RNA pTNT-Phlp 6.

Figure 12:
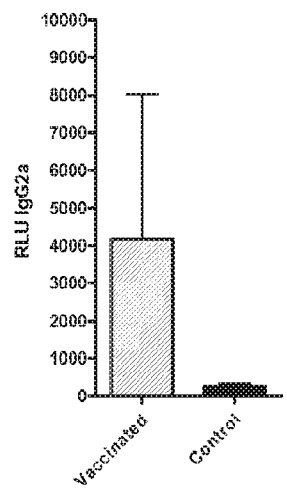
FIG. 12 shows the induction of Th 1 memory by RNA pTNT-Cor a 1.

FIG. 12 shows the induction of Th 1 memory by RNA pTNT-Cor a 1.

Figure 13:
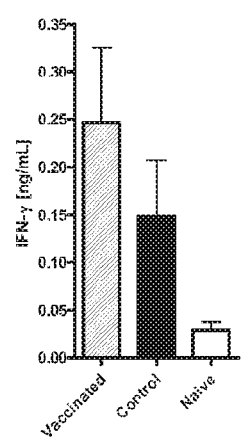
FIG. 13 shows the induction of Th 1 memory by RNA pTNT-Aln g 1.

FIG. 13 shows the induction of Th 1 memory by RNA pTNT-Aln g 1.

Figure 14A:
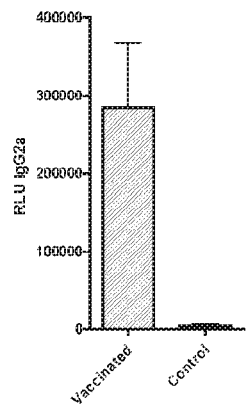
FIGS. 14A, 14B, and 14C show the induction of Th 1 memory and suppression of IgE responses by RNA pTNT-Fag s 1.
Figure 14B:
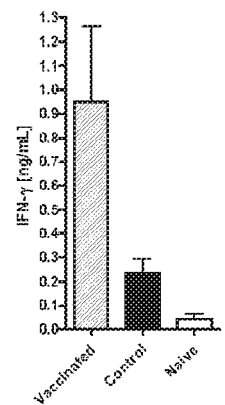
Figure 14C:
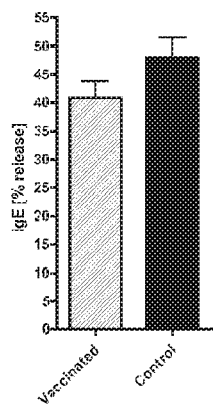

FIGS. 14A, 14B, and 14C show the induction of Th 1 memory and suppression of IgE responses by RNA pTNT-Fag s 1.

Figure 15A:
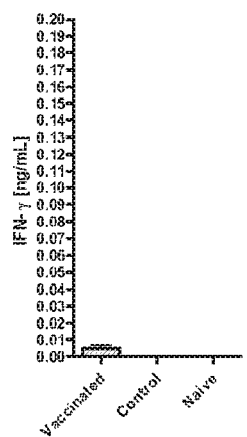
FIGS. 15A and 15B show the induction of Th 1 memory and suppression of IgE responses by RNA pTNT-Phlp 2.
Figure 15B:
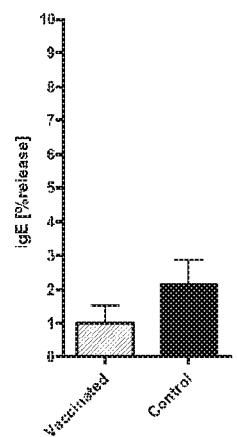

FIGS. 15A and 15B show the induction of Th 1 memory and suppression of IgE responses by RNA pTNT-Phlp 2.

FIGS. 16A and 16B show the induction of Th 1 memory and suppression of IgE responses by RNA pTNT-Phlp 7.

FIGS. 17A, 17B, and 17C show the induction of Th 1 memory and suppression of IgE responses by RNA pTNT-hybrid (Phlp 1-2-5-6).

FIGS. 18A and 18B show the induction of Th 1 memory by RNA pTNT-Cry j 1.

FIG. 19 shows the induction of Th 1 memory by RNA pTNT-Jun a 1.

FIG. 20 shows the induction of Th 1 memory by RNA pTNT-Amb a 1.

FIGS. 21A, 21B, and 21C show the induction of Th 1 memory and suppression of IgE responses by RNA pTNT-Api g 1.

FIGS. 22A and 22B show the induction of Th 1 memory by RNA pTNT-Dau c 1.

FIGS. 23A, 23B, and 23C show the induction of Th 1 memory and suppression of IgE responses by RNA pTNT-Mal d 1.

FIGS. 24A, 24B, and 24C show the induction of Th 1 memory and suppression of IgE responses by RNA pTNT-Ova.

FIGS. 25A and 25B show the induction of Th 1 memory and suppression of IgE responses by RNA pTNT-Beta-Casein.

FIG. 26 shows the induction of Th 1 memory responses by RNA pTNT-Cyp c 1.

FIGS. 27A and 27B show the induction of Th 1 memory responses by RNA pTNT-Fel d 1.

FIGS. 28A and 28B show the induction of Th 1 memory and suppression of IgE responses by RNA pTNT-Der p 2.

FIGS. 29A, 29B, and 29C show the induction of Th 1 memory and suppression of IgE responses by RNA pTNT-Alt a 1.

Figure 30A:
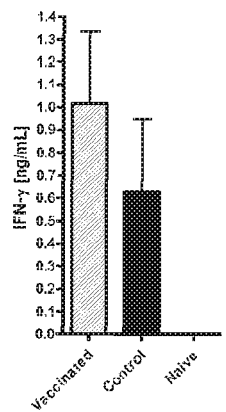
FIGS. 30A and 30B show the induction of Th 1 memory and suppression of IgE responses by RNA pTNT-Cla h 8.
Figure 30B:
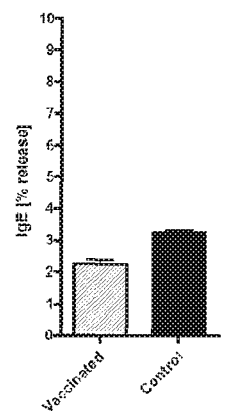

FIGS. 30A and 30B show the induction of Th 1 memory and suppression of IgE responses by RNA pTNT-Cla h 8.

Figure 31A:
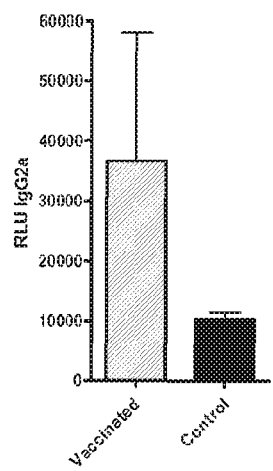
FIGS. 31A and 31B show the induction of Th 1 memory by RNA pTNT-Hev b 6.
Figure 31B:
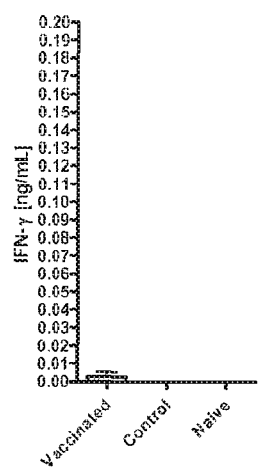

FIGS. 31A and 31B show the induction of Th 1 memory by RNA pTNT-Hev b 6.

Figure 32:
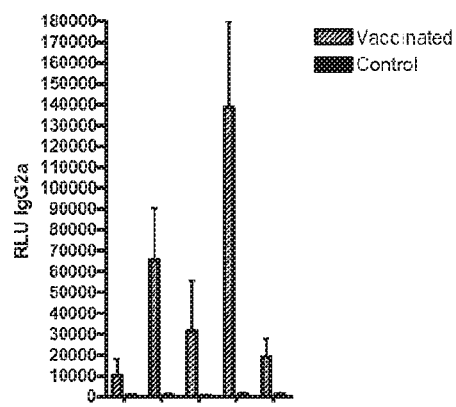
FIG. 32 shows the induction of Th 1 memory by RNA pTNT-hybrid (allergen).

FIG. 32 shows the induction of Th 1 memory by RNA pTNT-hybrid (allergen).

Figures 33A, 33B:
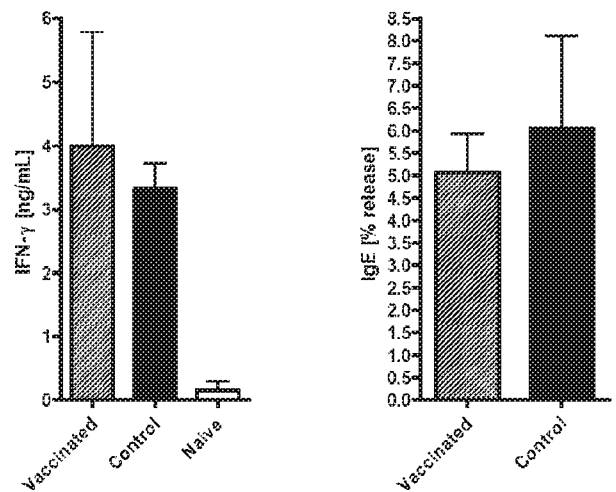
FIGS. 33A and 33B show the induction of Th 1 memory and suppression of IgE responses by RNA pTNT-Ara h 2.

FIGS. 33A and 3B show the induction of Th 1 memory and suppression of IgE responses by RNA pTNT-Ara h 2.

FIGS. 34A and 34B show the induction of Th 1 memory by RNA pTNT-Que a 1.

FIGS. 35A and 35B show no induction of Th 1 memory by RNA pTNT-Art v 1.

Figure 36A:
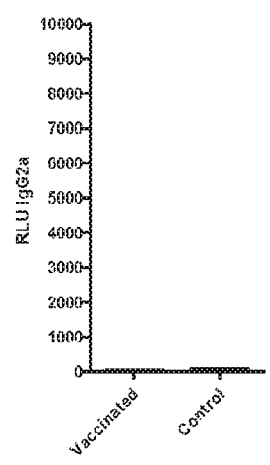
FIGS. 36A and 36B show no induction of Th 1 memory or suppression of IgE responses by RNA pTNT-Ole e 1.
Figure 36B:
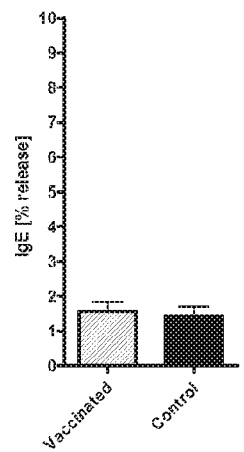

FIGS. 36A and 36B show no induction of Th 1 memory or suppression of IgE responses by RNA pTNT-Ole e 1.

EXAMPLES

Example 1

In the present example it is shown, that RNA as well as replicase-based RNA vaccines encoding the clinically relevant timothy grass pollen allergen Phlp 5 can effectively prevent from allergic responses.

Materials and Methods

Plasmids Used for RNA Transcription

Vector pTNT was purchased from Promega (Mannheim, Germany) and includes some special features providing advantages over other vectors. Two promoters, one for the SP6 and the other for the T7 polymerase, are present to allow SP6—as well as T7-based in vitro transcription. They lie in tandem adjacent to the multiple cloning site (MCS). A 5' β-globin leader sequence helps to increase the translation of several genes for a more rapid initiation of translation. Another feature to enhance gene expression is its synthetic poly(A)30 tail.

Vector pSin-Rep5 (Invitrogen, Austria) is derived from sindbis alphavirus, which is an enveloped, positive-stranded RNA virus. Alphavirus based replicon vectors lack viral structural proteins, but maintain the replication elements (replicase) necessary for cytoplasmic RNA self-amplification and expression of the inserted genes via an alphaviral promoter.

The Phlp 5 gene was excised from vector pCMV-Phlp5 via NheI/XbaI (Gabler et al. (2006), J Allergy Clin Immunol 118:734-741) and ligated into the XbaI restriction site of pTNT and pSin-Rep5 resulting in pTNT-P5 and pSin-Rep5-P5 respectively.

RNA Transcription

Plasmids pTNT-P5 and pSin-Rep5-P5 were linearised with the corresponding restriction enzymes; templates were purified via Phenol-Chloroform-Isoamylalcohol extraction, followed by a single Chloroform-Isoamylalcohol extraction. After addition of 1/10 volume of 3M Na-acetate pH 5.2 plasmids were precipitated with 2 volumes of 100% EtOH and washed 3 times with 70% EtOH.

All transcription reactions were performed with a T7 or SP6 RiboMAX™ Large Scale RNA Production Systems (Promega) according to the manufacturer's protocol. Briefly, for a 100 µl reaction, 20 µl Transcription buffer, 30 µl rNTPs, 5-10 µg template, and 10 µl Enzyme mix were filled up to 100 µl with Nuclease-free H2O and incubated for 2-3 h at 37° C. When using the SP6 RiboMax kit, 20 µl instead of 30 µl rNTPs were used.

To mimic the capped structure of mRNA, a 5'7-methyl guanosine nucleotide (m7G(5')ppp(5')G) or cap analog (EPICENTRE, USA) was incorporated during RNA synthesis. The rNTP mix was prepared as a 25:25:25:22.5:2.5 mM mix of rATP, rCTP, rUTP, rGTP and m7G(5')ppp(5')G.

Following transcription, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and resuspended in nuclease-free $H_2O$.

Results

In Vitro Transfection with RNA and Self-Replicating RNA

BHK-21 cells were transfected in vitro with two different RNA transcripts encoding β-galactosidase, either as conventional RNA vaccine transcribed from vector pTNT-βGal (βGal-RNA) or as self-replicating RNA transcribed from vector pRep5-f3Gal ((3Gal-repRNA).

RNA transcripts were tested with or without addition of a m7G(5')ppp(5')G cap structure. FIG. 1 shows that transfection with equal amounts of self replicating RNA induces a 7.5-fold higher expression of the transgene compared to conventional RNA. Additionally, stabilising RNA with a cap structure is essential for in vitro transfection/translation of RNA.

RNA-Based Vaccines Encoding the Allergen Phlp 5 are Immuno-Genic and Prevent from IgE Induction To investigate the potential of RNA-based vaccines to prevent from induction of allergy, female BALB/c mice were immunised with either conventional RNA endcoding Phl p 5 or self-replicating RNA encoding Phlp 5. To estimate the potency of the RNA vaccines also corresponding groups were immunised with the same doses of a conventional DNA vaccine (pCMV-P5) and a self-replicating DNA vaccine (pSin-P5) encoding Phlp 5. Mice were immunised three times in weekly intervals and two weeks later sensitised via two injections of recombinant Phlp 5 complexed with alum, a protocol known to induce an allergic phenotype, characterised by high levels of IgE and a TH2 biased cytokine profile of T cells.

FIG. 2A shows, that both RNA vaccines induce similar humoral immune responses compared to the self-replicating DNA vaccine pSin-P5. In contrast, the humoral immune response induced by the conventional DNA vaccine pCMV-P5 was approximately one order of magnitude higher compared to the other vaccines. All vaccine types displayed a clearly TH1 biased serological profile characterised by low IgG1/IgG2a ratios and no induction of functional IgE as measured by RBL release assay (FIG. 3, grey bars).

After sensitisation, the control group, that had not been pre-immunised, showed a strictly TH2 biased serology with high IgG1 levels and a high IgG1/IgG2a ratio, indicative of an allergic sensitisation. In contrast, all vaccinated groups maintained a TH1 balanced immunophenotype (FIG. 2B). Pre-vaccination with both types of RNA vaccines induced similar or better suppression of IgE induction compared to control animals as their DNA counterparts (FIG. 3, black bars). Overall, pre-vaccination with both types of RNA vaccines resulted in a 93% suppression of IgE induction upon allergic sensitisation.

RNA-Based Vaccines Induce a TH1 Biased T Cell Memory

Two weeks after the final sensitisation, splenocytes were re-stimulated in vitro with recombinant Phlp 5 protein to assess their TH1/TH2 profile. Therefore, the number of IFN-$\gamma$, IL-4, and IL-5 secreting cells was determined via ELISPOT.

All groups pre-vaccinated with nucleic acid vaccines showed significant induction of IFN-$\gamma$ secreting cells (FIG. 4A) compared to the control group. Simultaneously, the amount of cells secreting the TH2 type cytokines IL-4 (FIG. 4B) and IL-5 (FIG. 4C) were suppressed, indicating that similar to DNA vaccines, RNA vaccines could establish a TH1 biased antigen specific memory, that could be reactivated upon subsequent allergen exposure.

RNA-Based Vaccines Alleviate Allergen Induced Lung Inflammation

To investigate the effect of RNA-vaccination on the induction of lung pathology, two weeks after the last sensitisation, lung inflammation was induced by two daily i.n. applications of 1 µg recombinant Phl p 5. This protocol induced strong infiltration of leukocytes into the bronchoalveolar lavage fluid (BALF) of sensitised mice (FIG. 5A, control). Approximately 80% of the infiltrating leukocytes were eosinophils (FIG. 5B). In contrast, pre-vaccinated mice showed significantly reduced numbers of total leukocyte infiltrate, and an even greater reduction with respect to eosinophils.

The reduction of inflammatory infiltrate was also reflected by a strong suppression of IL-5 in the BALF (FIG. 6A). The suppression of IL-5 was inversely correlated with an induction of IFN-$\gamma$ FIG. 6B).

CONCLUSION

DNA vaccines hold great promise for prevention and treatment of allergic diseases. However, hypothetical risks associated with DNA vaccines question the use of this novel type of vaccine for clinical use in healthy adults or even children.

In this example it could be demonstrated for the first time, that naked RNA vaccination with a clinically relevant allergen can prevent from induction of allergy to the same extent as a comparable DNA vaccine applied at the same dosage.

To address the problem of producing larger quantities of RNA, conventional RNA was compared to self-replicating RNA derived from a Sindbis virus replicon. In vitro transfection with both types of RNA demonstrated that antigen expression depends among other factors on the addition of a m7G(5')ppp(5')G cap analogon. The majority of eukaryotic mRNAs is known to possess such a m7G(5')ppp(5')G cap structure at the 5'-end, which is important for binding translation initiation factors and contributes to mRNA stability. Additionally, it could be shown, that similar amounts of self-replicating RNA translate into 7-fold higher levels of proteins (FIG. 1), which can easily be attributed to the self-amplification of subgenomic RNA encoding the respective antigen. This is in contrast to self-replicating DNA vaccines, where protein expression is low compared to conventional DNA vaccines, an effect that has been attributed to the induction of apoptosis in transfected cells. Yet, the expression of RNA vaccines is only transient and therefore comparable to cells that undergo apoptosis shortly after transfection with self-replicating vaccines. Indeed self-replicating RNA vaccines induce similar humoral immune responses compared to self-replicating DNA vaccines (FIG. 2A), whereas the conventional DNA vaccine—with its continuous expression of antigen—displays the highest humoral immune response.

Although in the present example the self-replicating nucleic acid vaccines were applied at a five-fold reduced dose compared to conventional RNA/DNA vaccines, a similar induction of TH1 memory—indicated by a boost of IgG2a after subsequent sensitisation with recombinant allergen in alum (FIG. 2B) and a TH1 cytokine profile of re-stimulated splenocytes—as well as a high protective capability (FIG. 3)—were observed. Here, both RNA vaccines, and the self-replicating DNA vaccine show an even higher protective capacity than the conventional DNA vaccine, albeit the latter induces higher levels of intact antigen and higher humoral immune responses. This indicates that a vaccine induced long lasting secretion of the allergen may be counter-productive compared to short-term vaccine expression as seen with RNA and self-replicating vaccines.

RNA vaccination also resulted in a similar reduction of lung infiltration after i.n. provocation with allergen compared to DNA vaccines (FIG. 5A), which was mainly due to a drastic decrease in the amount of eosinophils in BALF (FIG. 5B). This correlated with a reduction of IL-5 (FIG. 6A) and induction of moderate levels of IFN-$\gamma$ (FIG. 2B) in the lung, indicating that the vaccine-induced generation of TH1 cells also affects the TH1/TH2 cytokine balance in the lung. Although in viral models IFN-$\gamma$ in the lung can have detrimental effects on asthma and lung pathology, this seems to be an indirect effect as IFN-$\gamma$ can activate lung epithelial cells to recruit more TH2 cells into the tissue. Indeed, in allergy models, it could be shown, that redirecting TH2 immunity towards a more balanced TH1 milieu has a beneficial effect on lung inflammation and airway hyperreactivity, mainly by counterregulating IL-5 and IL-13 (Ford, J. G. et al. (2001) J Immunol 167:1769-1777).

Taken together, it could be demonstrated, that RNA-based vaccines can induce significant protection from allergic sensitisation, and that by using self-replicating RNA-vaccines, this effect can be achieved at low doses. Given the excellent safety profile of RNA vaccines, this opens the door to clinical application of RNA vaccines not only in a therapeutic setting but also in healthy individuals with a high risk for development of allergic disorders.

Example 2

Materials and Methods
Plasmids and RNA Transcription

As described for example 1, the cDNA encoding Bet v 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Bet v 1 three times in weekly intervals and were sensitized one week later via two weekly injections of 1 µg recombinant Bet v 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Bet v 1 for 72 h and cell culture supernatants were analyzed for IFN-γ as an indicator of allergen-specific Th 1 cell activation Results Pre-vaccination with RNA pTNT-Bet v 1 (hatched bars) resulted in recruitment of allergen-specific Th1 cells as indicated by the increased induction of IgG2a (FIG. 7A) and secretion of IFN-γ (FIG. 7B) in contrast to sensitization controls (black bars) or naive mice (white bars). This Th 1 priming was able to suppress the induction of allergen specific IgE responses (FIG. 7C)

Example 3

Materials and Methods
Plasmids and RNA Transcription

As described for example 1, the cDNA encoding Car b 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Car b 1 three times in weekly intervals and were sensitized one week later via two weekly injections of 1 µg recombinant Car b 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Car b 1 for 72 h and cell culture supernatants were analyzed for IFN-γ as an indicator of allergen-specific Th 1 cell activation Results Pre-vaccination with RNA pTNT-Car b 1 (hatched bars) resulted in recruitment of allergen-specific Th1 cells as indicated by the increased induction of IgG2a (FIG. 8A) and secretion of IFN-γ (FIG. 8B) in contrast to sensitization controls (black bars) or naive mice (white bars). This Th 1 priming was able to suppress the induction of allergen specific IgE responses (FIG. 8C)

Example 4

Materials and Methods
Plasmids and RNA Transcription

As described for example 1, the cDNA encoding Cas s 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Cas s 1 three times in weekly intervals and were sensitized one week later via two weekly injections of 1 µg recombinant Cas s 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Cas s 1 for 72 h and cell culture supernatants were analyzed for IFN-γ as an indicator of allergen-specific Th 1 cell activation.

Results

Pre-vaccination with RNA pTNT-Cas s 1 (hatched bars) resulted in recruitment of allergen-specific Th 1 cells as indicated by the increased induction of IgG2a (FIG. 9A) and secretion of IFN-γ (FIG. 9B) in contrast to sensitization controls (black bars) or naive mice (white bars). This Th 1 priming was able to suppress the induction of allergen specific IgE responses (FIG. 9C)

Example 5

Materials and Methods
Plasmids and RNA Transcription

As described for example 1, the cDNA encoding Phlp 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Phlp 1 three times in weekly intervals and were sensitized one week later via two weekly injections of 1 µg recombinant Phlp 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA as described for experiment 1. Ten days after the final sensitization, splenocytes were re-stimulated in vitro with recombinant Phlp 1 for 72 h and cell culture supernatants were analyzed for IFN-γ as an indicator of allergen-specific Th 1 cell activation.

Results

Pre-vaccination with RNA pTNT-Phlp 1 (hatched bars) resulted in recruitment of allergen-specific Th 1 cells as indicated by the increased induction of IgG2a (FIG. 10A) and secretion of IFN-γ (FIG. 10B) in contrast to sensitization controls (black bars) or naive mice (white bars).

Example 6

Materials and Methods

Plasmids and RNA Transcription

As described for example 1, the cDNA encoding Phlp 6 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Phlp 6 three times in weekly intervals and were sensitized one week later via two weekly injections of 1 µg recombinant Phlp 6 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Phlp 6 for 72 h and cell culture supernatants were analyzed for IFN-γ as an indicator of allergen-specific Th 1 cell activation.

Results

Pre-vaccination with RNA pTNT-Phlp 6 (hatched bars) resulted in recruitment of allergen-specific Th1 cells as indicated by the increased induction of IgG2a (FIG. 11A) and secretion of IFN-γ (FIG. 11B) in contrast to sensitization controls (black bars) or naive mice (white bars). This Th 1 priming was able to suppress the induction of allergen specific IgE responses (FIG. 11C).

Example 7

Materials and Methods

Plasmids and RNA Transcription

As described for example 1, the cDNA encoding Cor a 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Cor a 1 three times in weekly intervals and were sensitized one week later via two weekly injections of 1 µg recombinant Cor a 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA.

Results

Pre-vaccination with RNA pTNT-Cor a 1 (hatched bars) resulted in recruitment of allergen-specific Th 1 cells as indicated by the increased induction of IgG2a (FIG. 12) in contrast to sensitization controls (black bars).

Example 8

Materials and Methods

Plasmids and RNA Transcription

As described for example 1, the cDNA encoding Aln g 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Aln g 1 three times in weekly intervals and were sensitized one week later via two weekly injections of 1 µg recombinant Aln g 1 complexed with alum to induce an allergic phenotype. Control animals were only sensitized and did not receive pre-vaccination with the RNA vaccine.

Measurement of Th 1 Memory Induction and Protection

Ten days after the final sensitization, splenocytes were re-stimulated in vitro with recombinant Aln g 1 for 72 h and cell culture supernatants were analyzed for IFN-γ as an indicator of allergen-specific Th 1 cell activation.

Results

Pre-vaccination with RNA pTNT-Aln g 1 (hatched bars) resulted in recruitment of allergen-specific Th 1 cells as indicated by the increased secretion of IFN-γ (FIG. 13) in contrast to sensitization controls (black bars) or naive mice (white bars).

Example 9

Materials and Methods

Plasmids and RNA Transcription

As described for example 1, the cDNA encoding Fag s 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Fag s 1 three times in weekly intervals and were sensitized one week later via two weekly injections of 1µg recombinant Fag s 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Fag s 1 for 72 h and cell culture supernatants were analyzed for IFN-γ as an indicator of allergen-specific Th 1 cell activation.

Results

Pre-vaccination with RNA pTNT-Fag s 1 (hatched bars) resulted in recruitment of allergen-specific Th 1 cells as indicated by the increased induction of IgG2a (FIG. 14A) and secretion of IFN-γ (FIG. 14B) in contrast to sensitization controls (black bars) or naive mice (white bars). This Th 1 priming was able to suppress the induction of allergen specific IgE responses (FIG. 14C).

Example 10

Materials and Methods
Plasmids and RNA Transcription

As described for example 1, the cDNA encoding Phlp 2 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Phlp 2 three times in weekly intervals and were sensitized one week later via two weekly injections of 1 µg recombinant Phlp 2 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgE was measured by RBL as described for experiment 1. Ten days after the final sensitization, splenocytes were re-stimulated in vitro with recombinant Phlp 2 for 72 h and cell culture supernatants were analyzed for IFN-γ as an indicator of allergen-specific Th 1 cell activation Results Pre-vaccination with RNA pTNT-Phlp 2 (hatched bars) resulted in recruitment of allergen-specific Th 1 cells as indicated by the increased secretion of IFN-γ (FIG. 15A) in contrast to sensitization controls (black bars) or naive mice (white bars). This Th1 priming was able to suppress the induction of allergen specific IgE responses (FIG. 15B).

Example 11

Materials and Methods
Plasmids and RNA Transcription

As described for example 1, the cDNA encoding Phlp 7 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Phlp 7 three times in weekly intervals and were sensitized one week later via two weekly injections of 1 µg recombinant Phlp 7 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgE was measured by RBL as described for experiment 1.

Results

Pre-vaccination with RNA pTNT-Phlp 7 (hatched bars) resulted in recruitment of allergen-specific Th 1 cells as indicated by the increased induction of IFN-γ (FIG. 16A) in contrast to sensitization controls (black bars) or naive mice (white bars). This Th 1 priming was able to suppress the induction of allergen specific IgE responses (FIG. 16B).

Example 12

Materials and Methods
Plasmids and RNA Transcription

As described for example 1, a hybrid cDNA encoding Phlp 1, Phlp 2, Phlp 5, and Phlp 6 (Linhart B. and Valenta R., Int Arch Allergy Immunol (2004) 134:324-331) was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-hybrid (Phlp 1-2-5-6) three times in weekly intervals and were sensitized one week later via two weekly injections of 1 µg recombinant Phlp 1, Phlp 2, Phlp 5, and Phlp 6 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant allergens for 72 h and cell culture supernatants were analyzed for IFN-γ as an indicator of allergen-specific Th 1 cell activation.

Results

Pre-vaccination with RNA pTNT-hybrid (Phlp 1-2-5-6) (hatched bars) resulted in recruitment of allergen-specific Th1 cells as indicated by the increased induction of IgG2a (FIG. 17A) and secretion of IFN-γ (FIG. 17B) in contrast to sensitization controls (black bars) or naive mice (white bars). This Th1 priming was able to suppress the induction of allergen specific IgE responses (FIG. 17C).

Example 13

Materials and Methods
Plasmids and RNA Transcription

As described for example 1, the cDNA encoding Cry j 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Cry j 1 three times in weekly intervals and were sensitized one week later via two weekly injections of 1μg recombinant Cry j 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a were measured by ELISA as described for experiment 1. Ten days after the final sensitization, splenocytes were re-stimulated in vitro with recombinant Cry j 1 for 72 h and cell culture supernatants were analyzed for IFN-γ as an indicator of allergen-specific Th 1 cell activation.

Results

Pre-vaccination with RNA pTNT-Cry j 1 (hatched bars) resulted in recruitment of allergen-specific Th1 cells as indicated by the increased induction of IgG2a (FIG. 18A) and secretion of IFN-γ (FIG. 18B) in contrast to sensitization controls (black bars) or naive mice (white bars).

Example 14

Materials and Methods
Plasmids and RNA Transcription

As described for example 1, the cDNA encoding Jun a 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Jun a 1 three times in weekly intervals and were sensitized one week later via two weekly injections of 1μg recombinant Jun a 1 complexed with alum to induce an allergic phenotype. Control animals were only sensitized and did not receive pre-vaccination with the RNA vaccine.

Measurement of Th 1 Memory Induction and Protection

Ten days after the final sensitization, splenocytes were re-stimulated in vitro with recombinant Jun a 1 for 72 h and cell culture supernatants were analyzed for IFN-γ as an indicator of allergen-specific Th 1 cell activation Results Pre-vaccination with RNA pTNT-Jun a 1 (hatched bars) resulted in recruitment of allergen-specific Th1 cells as indicated by the increased induction of IFN-γ (FIG. 19) in contrast to sensitization controls (black bars) or naive mice (white bars).

Example 15

Materials and Methods
Plasmids and RNA Transcription

As described for example 1, the cDNA encoding Amb a 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Amb a 1 three times in weekly intervals and were sensitized one week later via two weekly injections of 1 μg purified Amb a 1 complexed with alum to induce an allergic phenotype. Control animals were only sensitized and did not receive pre-vaccination with the RNA vaccine.

Measurement of Th 1 Memory Induction and Protection

Ten days after the final sensitization, splenocytes were re-stimulated in vitro with purified Amb a 1 for 72 h and cell culture supernatants were analyzed for IFN-γ as an indicator of allergen-specific Th 1 cell activation.

Results

Pre-vaccination with RNA pTNT-Amb a 1 (hatched bars) resulted in recruitment of allergen-specific Th1 cells as indicated by the increased secretion of IFN-γ (FIG. 20) in contrast to sensitization controls (black bars) or naive mice (white bars).

Example 16

Materials and Methods
Plasmids and RNA Transcription

As described for example 1, the cDNA encoding Api g 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Api g 1 three times in weekly intervals and were sensitized one week later via two weekly injections of 1μg recombinant Api g 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Api g 1 for 72 h and cell culture supernatants were analyzed for IFN-γ as an indicator of allergen-specific Th 1 cell activation.

Results

Pre-vaccination with RNA pTNT-Api g 1 (hatched bars) resulted in recruitment of allergen-specific Th 1 cells as indicated by the increased induction of IgG2a (FIG. 21A) and secretion of IFN-γ (FIG. 21B) in contrast to sensitization controls (black bars) or naive mice (white bars). This Th 1 priming was able to suppress the induction of allergen specific IgE responses (FIG. 21C)

Example 17

Materials and Methods
Plasmids and RNA Transcription

As described for example 1, the cDNA encoding Dau c 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Dau c 1 three times in weekly intervals and were sensitized one week later via two weekly injections of 1 μg recombinant Dau c 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA as described for experiment 1. Ten days after the final sensitization, splenocytes were re-stimulated in vitro with recombinant Dau c 1 for 72 h and cell culture supernatants were analyzed for IFN-γ as an indicator of allergen-specific Th 1 cell activation.

Results

Pre-vaccination with RNA pTNT-Dau c 1 (hatched bars) resulted in recruitment of allergen-specific Th 1 cells as indicated by the increased induction of IgG2a (FIG. 22A) and secretion of IFN-γ (FIG. 22B) in contrast to sensitization controls (black bars) or naive mice (white bars).

Example 18

Materials and Methods
Plasmids and RNA Transcription

As described for example 1, the cDNA encoding Mal d 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Mal d 1 three times in weekly intervals and were sensitized one week later via two weekly injections of 1 μg recombinant Mal d 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Mal d 1 for 72 h and cell culture supernatants were analyzed for IFN-γ as an indicator of allergen-specific Th 1 cell activation.

Results

Pre-vaccination with RNA pTNT-Mal d 1 (hatched bars) resulted in recruitment of allergen-specific Th 1 cells as indicated by the increased induction of IgG2a (FIG. 23A) and secretion of IFN-γ (FIG. 23B) in contrast to sensitization controls (black bars) or naive mice (white bars). This Th1 priming was able to suppress the induction of allergen specific IgE responses (FIG. 23C).

Example 19

Materials and Methods
Plasmids and RNA Transcription

As described for example 1, the cDNA encoding Ova was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Ova three times in weekly intervals and were sensitized one week later via two weekly injections of 1 μg recombinant Ova complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Ova for 72 h and cell culture supernatants were analyzed for IFN-γ as an indicator of allergen-specific Th 1 cell activation.

Results

Pre-vaccination with RNA pTNT-Ova (hatched bars) resulted in recruitment of allergen-specific Th1 cells as indicated by the increased induction of IgG2a (FIG. 24A) and secretion of IFN-γ (FIG. 24B) in contrast to sensitization controls (black bars) or naive mice (white bars). This Th 1 priming was able to suppress the induction of allergen specific IgE responses (FIG. 24C).

Example 20

Materials and Methods
Plasmids and RNA Transcription

As described for example 1, the cDNA encoding Beta-Casein was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Beta-Casein three times in weekly intervals and were sensitized one week later via two weekly injections of 1 μg recombinant Beta-Casein complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgE was measured by RBL as described for experiment 1. Ten days after the final sensitization, splenocytes were re-stimulated in vitro with recombinant Beta-Casein for 72 h and cell culture supernatants were analyzed for IFN-γ as an indicator of allergen-specific Th 1 cell activation Results Pre-vaccination with RNA pTNT-Beta-Casein (hatched bars) resulted in recruitment of allergen-specific Th 1 cells as indicated by the increased secretion of IFN-γ (FIG. 25A) in contrast to sensitization controls (black bars) or naive mice (white bars). This Th 1 priming was able to suppress the induction of allergen specific IgE responses (FIG. 25B).

Example 21

Materials and Methods
Plasmids and RNA Transcription

As described for example 1, the cDNA encoding Cyp c 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Cyp c 1 three times in weekly intervals and were sensitized one week later via two weekly injections of 1μg recombinant Cyp c 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA as described for experiment 1.

Results

Pre-vaccination with RNA pTNT-Cyp c 1 (hatched bars) resulted in recruitment of allergen-specific Th 1 cells as indicated by the increased induction of IgG2a (FIG. 26).

Example 22

Materials and Methods
Plasmids and RNA Transcription

As described for example 1, the cDNA encoding Fel d 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free $H_2O$.

Immunization and Sensitization

Mice were immunized with RNA pTNT-Fel d 1 three times in weekly intervals and were sensitized one week later via two weekly injections of 1 μg recombinant Fel d 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA as described for experiment 1. Ten days after the final sensitization, splenocytes were re-stimulated in vitro with recombinant Fel d 1 for 72 h and cell culture supernatants were analyzed for IFN-γ as an indicator of allergen-specific Th 1 cell activation.

Results

Pre-vaccination with RNA pTNT-Fel d 1 (hatched bars) resulted in recruitment of allergen-specific Th 1 cells as indicated by the increased induction of IgG2a (FIG. 27A) and secretion of IFN-γ (FIG. 27B) in contrast to sensitization controls (black bars) or naive mice (white bars).

Example 23

Materials and Methods
Plasmids and RNA Transcription

As described for example 1, the cDNA encoding Der p 2 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Der p 2 three times in weekly intervals and were sensitized one week later via two weekly injections of 1µg recombinant Der p 2 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1.

Results

Pre-vaccination with RNA pTNT-Der p 2 (hatched bars) resulted in recruitment of allergen-specific Th 1 cells as indicated by the increased induction of IgG2a (FIG. 28A). This Th 1 priming was able to suppress the induction of allergen specific IgE responses (FIG. 28B).

Example 24

Materials and Methods
Plasmids and RNA Transcription

As described for example 1, the cDNA encoding Alt a 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Alt a 1 three times in weekly intervals and were sensitized one week later via two weekly injections of 1 µg recombinant Alt a 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a and IgE were measured by ELISA and RBL as described for experiment 1. Ten days after the final sensitization, splenocytes were re-stimulated in vitro with recombinant Alt a 1 for 72 h and cell culture supernatants were analyzed for IFN-γ as an indicator of allergen-specific Th 1 cell activation.

Results

Pre-vaccination with RNA pTNT-Alt a 1 (hatched bars) resulted in recruitment of allergen-specific Th 1 cells as indicated by the increased induction of IgG2a (FIG. 29A) and secretion of IFN-γ (FIG. 29B) in contrast to sensitization controls (black bars) or naive mice (white bars). This Th 1 priming was able to suppress the induction of allergen specific IgE responses (FIG. 29C).

Example 25

Materials and Methods
Plasmids and RNA Transcription

As described for example 1, the cDNA encoding Cla h 8 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Cla h 8 three times in weekly intervals and were sensitized one week later via two weekly injections of 1 µg recombinant Cla h 8 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgE was measured RBL as described for experiment 1. Ten days after the final sensitization, splenocytes were re-stimulated in vitro with recombinant Cla h 8 for 72 h and cell culture supernatants were analyzed for IFN-γ as an indicator of allergen-specific Th 1 cell activation.

Results

Pre-vaccination with RNA pTNT-Cla h 8 (hatched bars) resulted in recruitment of allergen-specific Th 1 cells as indicated by the secretion of IFN-γ (FIG. 30A) in contrast to sensitization controls (black bars) or naive mice (white bars). This Th 1 priming was able to suppress the induction of allergen specific IgE responses (FIG. 30B).

Example 26

Materials and Methods
Plasmids and RNA Transcription

As described for example 1, the cDNA encoding Hev b 6 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization

Mice were immunized with RNA pTNT-Hev b 6 three times in weekly intervals and were sensitized one week later via two weekly injections of 1µg recombinant Hev b 6 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA as described for experiment 1. Ten days after the final sensitization, splenocytes were re-stimulated in vitro with recombinant Hev b 6 for 72 h and cell culture supernatants were analyzed for IFN-γ as an indicator of allergen-specific Th 1 cell activation Results Pre-vaccination with RNA pTNT-Hev b 6 (hatched bars) resulted in recruitment of allergen-specific Th 1 cells as indicated by the increased induction of IgG2a (FIG. 31A)

and secretion of IFN-γ (FIG. 31B) in contrast to sensitization controls (black bars) or naive mice (white bars).

Example 27

Materials and Methods
Plasmids and RNA Transcription
As described for example 1, a hybrid cDNA encoding parts of 5 different allergens was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization
Mice were immunized with RNA pTNT-hybrid (Aln-Cor-Que-Car-Bet) three times in weekly intervals and were sensitized one week later via two weekly injections of 1 µg recombinant whole allergens complexed with alum to induce an allergic phenotype. Control animals were only sensitized and did not receive pre-vaccination with the RNA vaccine.

Measurement of Th 1 Memory Induction and Protection
One week after the last sensitization, allergen specific serum IgG2a was measured by ELISA as described for experiment 1.

Results
Pre-vaccination with RNA pTNT-hybrid (allergen) (hatched bars) resulted in recruitment of allergen-specific Th 1 cells as indicated by the increased induction of IgG2a (FIG. 32).

Example 28

Materials and Methods
Plasmids and RNA Transcription
As described for example 1, the cDNA encoding Ara h 2 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization
Mice were immunized with RNA pTNT-Ara h 2 three times in weekly intervals and were sensitized one week later via two weekly injections of 1 µg recombinant Ara h 2 complexed with alum to induce an allergic phenotype. Control animals were only sensitized and did not receive pre-vaccination with the RNA vaccine.

Measurement of Th 1 Memory Induction and Protection
One week after the last sensitization, allergen specific serum IgE was measured by ELISA and RBL as described for experiment 1. Ten days after the final sensitization, splenocytes were re-stimulated in vitro with recombinant Ara h 2 for 72 h and cell culture supernatants were analyzed for IFN-γ as an indicator of allergen-specific Th 1 cell activation.

Results
Pre-vaccination with RNA pTNT-Ara h 2 (hatched bars) resulted in recruitment of allergen-specific Th 1 cells as indicated by the secretion of IFN-γ (FIG. 33A). This Th 1 priming was able to suppress the induction of allergen specific IgE responses (FIG. 33B).

Example 29

Materials and Methods
Plasmids and RNA Transcription
As described for example 1, the cDNA encoding Que a 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization
Mice were immunized with RNA pTNT-Que a 1 three times in weekly intervals and were sensitized one week later via two weekly injections of 1 µg recombinant Que a 1 complexed with alum to induce an allergic phenotype. Control animals were only sensitized and did not receive pre-vaccination with the RNA vaccine.

Measurement of Th 1 Memory Induction and Protection
One week after the last sensitization, allergen specific serum IgG2a was measured by ELISA as described for experiment 1. Ten days after the final sensitization, splenocytes were re-stimulated in vitro with recombinant Que a 1 for 72 h and cell culture supernatants were analyzed for IFN-γ as an indicator of allergen-specific Th 1 cell activation Results
Pre-vaccination with RNA pTNT-Que a 1 (hatched bars) resulted in recruitment of allergen-specific Th 1 cells as indicated by the increased induction of IgG2a (FIG. 34A) and secretion of IFN-γ (FIG. 34B) in contrast to sensitization controls (black bars) or naive mice (white bars).

Example 30

Materials and Methods
Plasmids and RNA Transcription
As described for example 1, the cDNA encoding Art v 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H$_2$O.

Immunization and Sensitization
Mice were immunized with RNA pTNT-Art v 1 three times in weekly intervals and were sensitized one week later via two weekly injections of 1µg recombinant Art v 1 complexed with alum to induce an allergic phenotype. Control animals were only sensitized and did not receive pre-vaccination with the RNA vaccine.

Measurement of Th 1 Memory Induction and Protection

One week after the last sensitization, allergen specific serum IgG2a was measured by ELISA and RBL as described for experiment 1. Ten days after the final sensitization, splenocytes were re-stimulated in vitro with recombinant Art v 1 for 72 h and cell culture supernatants were analyzed for IFN-γ as an indicator of allergen-specific Th 1 cell activation Measurement of Th 1 Memory Induction and Protection One week after the last sensitization, allergen specific serum IgG2a and IgE were measured by ELISA and RBL as described for example 1.

Results

Pre-vaccination with RNA pTNT-Ole e 1 (hatched bars) resulted in no recruitment of allergen-specific Th 1 cells as indicated by no increased induction of IgG2a (FIG. 36A). Furthermore, no suppression of the induction of allergen specific IgE responses could be measured (FIG. 36B).

```
                        SEQUENCE LISTING

<160> NUMBER OF SEQ ID NOS: 1

<210> SEQ ID NO 1
<211> LENGTH: 90
<212> TYPE: PRT
<213> ORGANISM: Dermatophagoides pteronyssinus

<400> SEQUENCE: 1

Met Lys Phe Asn Ile Ile Ile Val Phe Ile Ser Leu Ala Ile Leu Val
1               5                   10                  15

His Ser Ser Tyr Ala Ala Asn Asp Asn Asp Asp Pro Thr Thr Thr
            20                  25                  30

Val His Pro Thr Thr Thr Glu Gln Pro Asp Asp Lys Phe Glu Cys Pro
        35                  40                  45

Ser Arg Phe Gly Tyr Phe Ala Asp Pro Lys Asp Pro His Lys Phe Tyr
    50                  55                  60

Ile Cys Ser Asn Trp Glu Ala Val His Lys Asp Cys Pro Gly Asn Thr
65                  70                  75                  80

Arg Trp Asn Glu Asp Glu Glu Thr Cys Thr
                85                  90
```

Results

Pre-vaccination with RNA pTNT-Art v 1 (hatched bars) resulted in no recruitment of allergen-specific Th 1 cells as indicated by no increased induction of IgG2a (FIG. 35A) or secretion of IFN-γ (FIG. 35B).

Example 31

Materials and Methods

Plasmids and RNA Transcription

As described for example 1, the cDNA encoding Ole e 1 was cloned into vector pTNT. RNA transcripts were prepared as described and capped using a ScriptCap kit (Ambion) according to the manufacturer's protocol.

Capped transcripts were incubated with RNAse free DNAse (Promega) for 15 min at 37° C. to remove template DNA. Subsequently, RNA was precipitated by adding 1 volume of 5M ammonium acetate to the reaction tube and incubating the mixture for 10-15 minutes on ice. After a centrifugation period of 15 minutes (13000 rpm) at 4° C. or room temperature, the pellet was washed with 70% ethanol and re-suspended in nuclease free H₂O.

Immunization and Sensitization

Mice were immunized with RNA pTNT-Ole e 1 three times in weekly intervals and were sensitized one week later via two weekly injections of 1μg recombinant Ole e 1 complexed with alum to induce an allergic phenotype. Control animals were only sensitized and did not receive pre-vaccination with the RNA vaccine.

We claim:

1. A method for inducing a TH1-biased immune response in a subject, comprising administering to the subject a composition comprising: an RNA molecule and an adjuvant comprising one or more cytokine, wherein the RNA molecule encodes an allergen selected from the group consisting of Aln g 1, Alt a 1, Amb a 1, Api g 1, Ara h 2, Bet v 1, beta-casein, Car b 1, Cas s 1, Cla h 8, Cor a 1, Cry j 1, Cyp c 1, Dau c 1, Der p 2, Fag s 1, Fel d 1, Hey b 6, Jun a 1, Mal d 1, ovalbumin (OVA), Phl p 1, Phl p 2, Phl p 5, Phl p 6, Phl p 7, and hypoallergenic fragments thereof, and wherein the RNA molecule optionally further has an RNA sequence encoding a peptide, polypeptide or protein and/or at least one element selected from the group consisting of replicase, 1-globin leader sequence, cap0, cap1 and poly A tail and the one or more cytokine is selected from the group consisting of IL-2, IL-3, IL-12, IL-15, IL-18, IFN-gamma, IL-10, TGF-beta, granulocyte-macrophage (GM)-colony stimulating factor (CSF) and macrophage inflammatory factor.

2. The method according to claim 1, comprising administering the composition by intramuscular, intradermal, intravenous, transdermal, topical or biolistic route.

3. The method according to claim 1, wherein the composition consists of the RNA molecule, water and one or more cytokine selected from the group consisting of IL-2, IL-3, IL-12, IL-15, IL-18, IFN-gamma, IL-10, TGF-beta, granulocyte-macrophage (GM)-colony stimulating factor (CSF) and macrophage inflammatory factor.

4. The method according to claim 1, wherein the RNA molecule encoding the allergen further has an RNA sequence encoding a peptide, polypeptide or protein.

5. The method according to claim 1, wherein the RNA molecule further has at least one element selected from the group consisting of replicase, 1-globin leader sequence, cap0, cap1 and poly A tail.

6. The method according to claim 1, wherein said cytokine is IL-12.

7. The method according to claim 1, wherein said cytokine is IL-15.

8. A method for inducing a TH1-biased immune response in a subject, comprising administering to the subject a composition comprising an RNA molecule suspended in water and an adjuvant comprising one or more cytokine, wherein the RNA molecule encodes an allergen selected from the group consisting of Aln g 1, Alt a 1, Amb a 1, Api g 1, Ara h 2, Bet v 1, beta-casein, Car b 1, Cas s 1, Cla h 8, Cor a 1, Cry j 1, Cyp c 1, Dau c 1, Der p 2, Fag s 1, Fel d 1, Hey b 6, Jun a 1, Mal d 1, ovalbumin (OVA), Phl p 1, Phl p 2, Phl p 5, Phl p 6, Phl p 7, hypoallergenic fragments thereof, wherein the RNA molecule optionally further has an RNA sequence encoding a peptide, polypeptide or protein and/or at least one element selected from the group consisting of replicase, 1-globin leader sequence, cap0, cap1 and poly A tail, wherein said one or more cytokine is selected from the group consisting of IL-2, IL-3, IL-12, IL-15, IL-18, IFN-gamma, IL-10, TGF-beta, granulocyte-macrophage (GM)-colony stimulating factor (CSF) and macrophage inflammatory factor, and wherein administering the composition induces in the subject the TH1-biased immune response.

9. The method according to claim 8, comprising administering the composition by intramuscular, intradermal, intravenous, transdermal, topical or biolistic route.

10. The method according to claim 8, wherein the composition consists of the RNA molecule, water and one or more cytokine selected from the group consisting of IL-2, IL-3, IL-12, IL-15, IL-18, IFN-gamma, IL-10, TGF-beta, granulocyte-macrophage (GM)-colony stimulating factor (CSF) and macrophage inflammatory factor.

11. The method according to claim 8, wherein the RNA molecule encodes the allergen and a peptide, polypeptide or protein.

12. The method according to claim 8, wherein the RNA molecule has at least one element selected from the group consisting of replicase, 1-globin leader sequence, cap0, cap1 and poly A tail.

13. The method according to claim 8, wherein said cytokine is IL-12.

14. The method according to claim 8, wherein said cytokine is IL-15.

* * * * *